(12) United States Patent
Fyfe

(10) Patent No.: US 8,927,563 B2
(45) Date of Patent: Jan. 6, 2015

(54) KINASE INHIBITOR

(71) Applicants: Respivert Limited, Buckinghamshire (GB); Topivert Pharma Limited, London (GB)

(72) Inventor: Matthew Colin Thor Fyfe, London (GB)

(73) Assignees: Respivert Limited, Buckinghamshire (GB); Topivert Pharma Limited, London (GB)

( * ) Notice: Subject to any disclaimer, the term of this patent is extended or adjusted under 35 U.S.C. 154(b) by 0 days.

(21) Appl. No.: 14/242,531

(22) Filed: Apr. 1, 2014

(65) Prior Publication Data
US 2014/0296271 A1  Oct. 2, 2014

(30) Foreign Application Priority Data

Apr. 2, 2013  (GB) .................... 1305945.6
Dec. 20, 2013  (GB) .................... 1322678.2
Feb. 14, 2014  (GB) .................... 1402647.0

(51) Int. Cl.
| | |
|---|---|
| C07D 239/47 | (2006.01) |
| A61K 31/506 | (2006.01) |
| A61K 31/5377 | (2006.01) |
| C07D 211/86 | (2006.01) |
| A61K 31/44 | (2006.01) |
| C07D 405/12 | (2006.01) |
| C07D 405/14 | (2006.01) |
| A61K 31/444 | (2006.01) |
| A61K 31/4427 | (2006.01) |
| A61K 31/505 | (2006.01) |
| A61K 31/541 | (2006.01) |
| A61K 31/551 | (2006.01) |
| A61K 31/553 | (2006.01) |
| C07C 311/08 | (2006.01) |
| C07D 403/12 | (2006.01) |
| C07D 213/74 | (2006.01) |
| C07D 401/12 | (2006.01) |
| C07D 413/12 | (2006.01) |

(52) U.S. Cl.
CPC .......... *A61K 31/5377* (2013.01); *C07D 239/47* (2013.01); *C07D 211/86* (2013.01); *A61K 31/44* (2013.01); *A61K 31/506* (2013.01); *C07D 405/12* (2013.01); *C07D 405/14* (2013.01); *A61K 31/444* (2013.01); *A61K 31/4427* (2013.01); *A61K 31/505* (2013.01); *A61K 31/541* (2013.01); *A61K 31/551* (2013.01); *A61K 31/553* (2013.01); *C07C 311/08* (2013.01); *C07D 403/12* (2013.01); *C07D 213/74* (2013.01); *C07D 401/12* (2013.01); *C07D 413/12* (2013.01)
USPC .......................................... 514/272; 544/321

(58) Field of Classification Search
USPC .......................................... 544/321; 514/272
See application file for complete search history.

(56) References Cited

U.S. PATENT DOCUMENTS 6,319,921 B1   11/2001  Cirillo et al.
6,492,393 B1   12/2002  Breitfelder et al.
(Continued)

FOREIGN PATENT DOCUMENTS

EP    2 578 582 A1    4/2013
WO    WO 98/52558     11/1998
(Continued)

OTHER PUBLICATIONS

Robinson, Medical Therapy of Inflammatory Bowel Disease for the 21st Century, Eur J Surg, Suppl582, pp. 90-98 (1998).*
(Continued)

*Primary Examiner* — Deepak Rao
(74) *Attorney, Agent, or Firm* — Knobbe, Martens, Olson & Bear, LLP

(57) ABSTRACT

There is provided a compound of formula I,

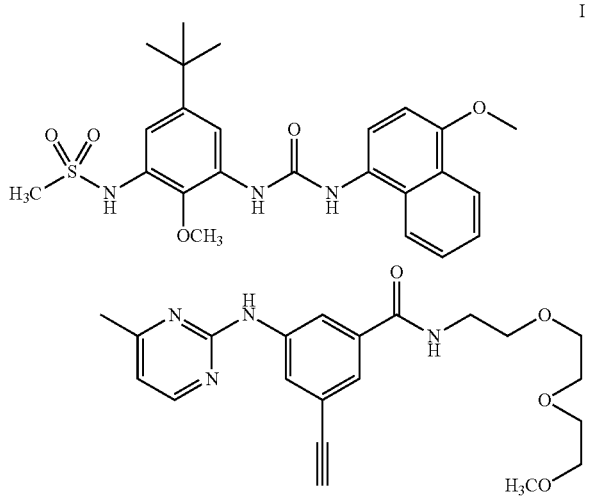

which compound has antiinflammatory activity (e.g. through inhibition of one or more of members of: the family of p38 mitogen-activated protein kinase enzymes; Syk kinase; and members of the Src family of tyrosine kinases, e.g., Src and Lck) and has use in therapy, including in pharmaceutical combinations, especially in the treatment of inflammatory diseases, including inflammatory diseases of the lung, eye and intestines.

6 Claims, No Drawings

(56) References Cited

U.S. PATENT DOCUMENTS

| | | |
|---|---|---|
| 6,492,529 B1 | 12/2002 | Kapadia et al. |
| 6,525,046 B1 | 2/2003 | Cirillo et al. |
| 6,852,717 B2 | 2/2005 | Cirillo et al. |
| 6,872,726 B2 | 3/2005 | Cirillo et al. |
| 6,894,173 B2 | 5/2005 | Zhang et al. |
| 6,916,814 B2 | 7/2005 | Moss et al. |
| 7,241,758 B2 | 7/2007 | Hoa et al. |
| 7,279,475 B2 | 10/2007 | Cirillo et al. |
| 7,652,022 B2 | 1/2010 | Floersheimer et al. |
| 7,838,541 B2 | 11/2010 | Dumas et al. |
| 8,293,748 B2 | 10/2012 | Ito et al. |
| 8,293,771 B2 | 10/2012 | Ito et al. |
| 8,299,073 B2 | 10/2012 | Ito et al. |
| 8,299,074 B2 | 10/2012 | Ito et al. |
| 8,618,140 B2 | 12/2013 | Ito et al. |
| 8,642,773 B2 | 2/2014 | Ito et al. |
| 2001/0011135 A1 | 8/2001 | Riedl et al. |
| 2004/0152725 A1 | 8/2004 | Moss et al. |
| 2005/0014753 A1 | 1/2005 | Ding et al. |
| 2008/0312192 A1 | 12/2008 | Bold et al. |
| 2012/0244120 A1 | 9/2012 | Charron et al. |
| 2013/0029990 A1 | 1/2013 | King-Underwood et al. |
| 2013/0040962 A1 | 2/2013 | King-Underwood et al. |
| 2013/0040995 A1 | 2/2013 | King-Underwood et al. |
| 2013/0102607 A1 | 4/2013 | Cass et al. |
| 2013/0123260 A1 | 5/2013 | Charron et al. |
| 2013/0156826 A1 | 6/2013 | Murray et al. |
| 2014/0057915 A1 | 2/2014 | Cariou et al. |

FOREIGN PATENT DOCUMENTS

| | | |
|---|---|---|
| WO | WO 99/23091 | 5/1999 |
| WO | WO 00/41698 | 7/2000 |
| WO | WO 00/42012 | 7/2000 |
| WO | WO 00/43384 | 7/2000 |
| WO | WO 00/55139 | 9/2000 |
| WO | WO 01/04115 | 1/2001 |
| WO | WO 01/36403 | 5/2001 |
| WO | WO 02/083628 | 10/2002 |
| WO | WO 02/083642 | 10/2002 |
| WO | WO 02/092576 | 11/2002 |
| WO | WO 02/096876 | 12/2002 |
| WO | WO 03/005999 | 1/2003 |
| WO | WO 03/068223 | 8/2003 |
| WO | WO 03/068228 | 8/2003 |
| WO | WO 03/072569 | 9/2003 |
| WO | WO 03/099771 | 12/2003 |
| WO | WO 2004/014870 | 2/2004 |
| WO | WO 2005/023761 | 3/2004 |
| WO | WO 2004/089286 | 10/2004 |
| WO | WO 2004/113352 | 12/2004 |
| WO | WO 2005/005396 | 1/2005 |
| WO | WO 2005/018624 | 3/2005 |
| WO | WO 2005/044825 | 5/2005 |
| WO | WO 2005/051366 | 6/2005 |
| WO | WO 2006/015775 | 2/2006 |
| WO | WO 2006/043090 | 4/2006 |
| WO | WO 2007/004749 | 1/2007 |
| WO | WO 2007/053394 | 5/2007 |
| WO | WO 2010/038085 | 4/2010 |
| WO | WO 2010/038086 | 4/2010 |
| WO | WO 2010/067130 | 6/2010 |
| WO | WO 2010/067131 | 6/2010 |
| WO | WO 2010/112936 | 10/2010 |
| WO | WO 2011/070368 | 6/2011 |
| WO | WO 2011/070369 | 6/2011 |
| WO | WO 2011/121366 | 10/2011 |
| WO | WO 2011/124923 | 10/2011 |
| WO | WO 2011/124930 | 10/2011 |
| WO | WO 2011/154738 | 12/2011 |
| WO | WO 2011/158039 | 12/2011 |
| WO | WO 2011/158042 | 12/2011 |
| WO | WO 2011/158044 | 12/2011 |
| WO | WO 2013/050756 | 4/2013 |
| WO | WO 2013/050757 | 4/2013 |
| WO | WO 2014/027209 | 2/2014 |
| WO | WO 2014/033446 | 3/2014 |
| WO | WO 2014/033447 | 3/2014 |
| WO | WO 2014/033448 | 3/2014 |
| WO | WO 2014/033449 | 3/2014 |
| WO | WO 2014/076484 | 5/2014 |

OTHER PUBLICATIONS

Singh et al., Immune therapy in inflammatory bowel disease and models of colitis, British Journal of Surgery, 88, 1558-1569 (2001).*
Patterson et al., Protein kinase inhibitors in the treatment of inflammatory and autoimmune diseases, Clinical and Experimental Immunology, 176(1), pp. 1-10, 2014.*
U.S. Appl. No. 14/242,741, filed Apr. 1, 2014, Baker et al.
Badrinarayan, et al. 2011 "Sequence, structure, and active site analyses of p38 MAP kinase: Exploiting DFG-out conformation as a strategy to design new type II leads" *Journal of Chemical Information and Modeling* 51; 115-129.
Barnes, et al. 2007 "Trimethylsilylpyrazoles as novel inhibitors of p38 MAP kinase: A new use of silicon bioisosteres in medicinal chemistry" *Bioorganic & Medicinal Chemistry* 17; 354-357.
Cirillo, et al. 2009 "Discovery and characterization of the N-phenyl-N'-naphthylurea class of p38 kinase inhibitors" *Bioorganic & Medicinal Chemistry* 19; 2386-2391.
Cogan, et al. 2008 "Structure-based design and subsequent optimization of 2-tolyl-(1,2,3-triazol-1-yl-4-carboxamide) inhibitors of p38 MAP kinase" *Bioorganic & Medicinal Chemistry* 18; 3251-3255.
Dietrich, et al. 2010 "The design, synthesis, and evaluation of 8 hybrid DFG-out allosteric kinase inhibitors: A structural analysis of the binding interactions of Gleevec®, Nexavar®, and BIRB-796" *Bioorganic & Medicinal Chemistry* 18; 5738-5748.
Dumas, et al. 2004 "Recent developments in the discovery of protein kinase inhibitors from the urea class" *Current Opinion in Drug Discovery & Development* 7(5); 600-616.
Goldberg, et al. 2007 "Discovery and Optimization of p38 Inhibitors via Computer-Assisted Drug Decision" *Journal of Medicinal Chemistry* 50; 4016-4026.
Menard, et al. 2009 "Novel potent BRAF inhibitors: Toward 1 nM compounds through optimization of the Central Phenyl Ring" *Journal of Medicinal Chemistry* 52; 3881-3891.
Montalban, et al. 2010 "KR-003048, a potent, orally active inhibitors of p38 mitogen-activated protein kinase" *European Journal of Pharmacology* 632; 93-102.
Montalban, et al. 2010 "Optimization of α-ketoamide based p38 inhibitors through modifications to the region that binds to the allosteric site" *Bioorganic & Medicinal Chemistry* 20; 4819-4824.
Pettus, et al. 2008 "Small Molecule p38 MAP Kinase Inhibitors for the Treatment of Inflammatory Diseases: Novel Structures and Developments During 2006-2008" *Current Topics in Medicinal Chemistry* 8; 1452-1467.
CAS Registry No. 1379397-83-7, 2012 American Chemical Society.
CAS Registry No. 1384608-34-7, 2012 American Chemical Society.
Zambon, et al. 2010 "Novel hinge binder improves activity and pharmacokinetic properties of BRAF inhibitors" *Journal of Medicinal Chemistry* 53; 5639-5655.

* cited by examiner

KINASE INHIBITOR

FIELD OF THE INVENTION

This invention relates, inter alia, to a compound which is an antiinflammatory agent (e.g. through inhibition of one or more members of: the family of p38 mitogen-activated protein kinase enzymes (referred to herein as p38 MAP kinase inhibitors), for example the alpha kinase sub-type thereof; Syk kinase; and the Src family of tyrosine kinases). The invention also relates to the use of such compound in therapy, including in mono- and combination therapies, especially in the treatment of inflammatory diseases, including inflammatory diseases of the lung (such as asthma and chronic obstructive pulmonary disease (COPD)), eye (such as uveitis and keratoconjunctivitis sicca (dry eye)) and gastrointestinal tract (such as Crohn's disease and ulcerative colitis).

BACKGROUND OF THE INVENTION

The listing or discussion of an apparently prior-published document in this specification should not necessarily be taken as an acknowledgement that the document is part of the state of the art or is common general knowledge.

Four p38 MAPK isoforms (alpha, beta, gamma and delta respectively) have been identified, each displaying different patterns of tissue expression. The p38 MAPK alpha and beta isoforms are found ubiquitously throughout the body, are present in many different cell types and are inhibited by a number of previously described small molecular weight compounds.

Early classes of inhibitors were highly toxic due to the broad tissue distribution of these isoforms which resulted in off-target effects of the compounds. Some of the more recently identified inhibitors show improved selectivity for p38 MAPK alpha and beta isoforms and have wider safety margins.

p38 MAP kinase is believed to play a pivotal role in many of the signalling pathways that are involved in initiating and maintaining chronic, persistent inflammation in human disease, for example, in severe asthma, COPD and inflammatory bowel disease (IBD). There is now an abundant literature which demonstrates that p38 MAP kinase is activated by a range of pro-inflammatory cytokines and that its activation results in the recruitment and release of further pro-inflammatory cytokines. Indeed, data from some clinical studies demonstrate beneficial changes in disease activity in patients during treatment with p38 MAP kinase inhibitors. For instance, Smith describes the inhibitory effect of p38 MAP kinase inhibitors on TNFα (but not IL-8) release from human PBMCs (Smith, S. J., *Br. J. Pharmacol.*, 2006, 149:393-404).

The use of inhibitors of p38 MAP kinase in the treatment of COPD and IBD has also been proposed. Small molecule inhibitors targeted to p38 MAPKα/β have proven to be effective in reducing various parameters of inflammation in:
  cells and tissues obtained from patients with COPD, who are generally corticosteroid insensitive (Smith, S. J., *Br. J. Pharmacol.*, 2006, 149:393-404);
  biopsies from IBD patients (Docena, G. et al., *J. Trans. Immunol.*, 2010, 162:108-115); and in vivo animal models (Underwood, D. C. et al., *Am. J. Physiol.*, 2000, 279:L895-902; Nath, P. et al., *Eur. J. Pharmacol.*, 2006, 544:160-167).

Irusen and colleagues also suggested the possibility of involvement of p38 MAPKα/β on corticosteroid insensitivity via the reduction of binding affinity of the glucocorticoid receptor (GR) in nuclei (Irusen, E. et al., *J. Allergy Clin. Immunol.*, 2002, 109:649-657). Clinical investigations in inflammatory diseases with a range of p38 MAP kinase inhibitors, including AMG548, BIRB796, VX702, SCIO469 and SCIO323, have been described (Lee, M. R. and Dominguez, C., *Current Med. Chem.*, 2005, 12:2979-2994). However, the major obstacle hindering the utility of p38 MAP kinase inhibitors in the treatment of human chronic inflammatory diseases has been the toxicity observed in patients. This has been sufficiently severe to result in the withdrawal from clinical development of many of the compounds progressed, including all those specifically mentioned above.

COPD is a condition in which the underlying inflammation is reported to be substantially resistant to the anti-inflammatory effects of inhaled corticosteroids. Consequently, a superior strategy for treating COPD would be to develop an intervention which has both inherent anti-inflammatory effects and the ability to increase the sensitivity of the lung tissues of COPD patients to inhaled corticosteroids. The recent publication of Mercado et al. (2007; *American Thoracic Society Abstract* A56) demonstrates that silencing p38 MAPK γ has the potential to restore sensitivity to corticosteroids. Thus, there may be a dual benefit for patients in the use of a p38 MAP kinase inhibitor for the treatment of COPD.

Many patients diagnosed with asthma or with COPD continue to suffer from uncontrolled symptoms and from exacerbations of their medical condition that can result in hospitalisation. This occurs despite the use of the most advanced, currently available treatment regimens, comprising of combination products of an inhaled corticosteroid and a long acting β-agonist. Data accumulated over the last decade indicates that a failure to manage effectively the underlying inflammatory component of the disease in the lung is the most likely reason that exacerbations occur. Given the established efficacy of corticosteroids as anti-inflammatory agents and, in particular, of inhaled corticosteroids in the treatment of asthma, these findings have provoked intense investigation. Resulting studies have identified that some environmental insults invoke corticosteroid-insensitive inflammatory changes in patients' lungs. An example is the response arising from virally-mediated upper respiratory tract infections (URTI), which have particular significance in increasing morbidity associated with asthma and COPD.

It has been disclosed previously that compounds that inhibit the activity of both the c-Src and Syk kinases are effective agents against rhinovirus replication (Charron, C. E. et al., WO 2011/158042) and that compounds that inhibit p59-HCK are effective against influenza virus replication (Charron, C. E. et al., WO 2011/070369). Taken together with inhibition of p38 MAPK, these are particularly attractive properties for compounds to possess that are intended to treat patients with chronic respiratory diseases.

Certain p38 MAPK inhibitors have also been described as inhibitors of replication of respiratory syncytial virus (Cass L. et al., WO 2011/158039).

The precise etiology of IBD is uncertain, but is believed to be governed by genetic and environmental factors that interact to promote an excessive and poorly controlled mucosal inflammatory response directed against components of the luminal microflora. This response is mediated through infiltration of inflammatory neutrophils, dendritic cells and T-cells from the periphery. p38 has become an obvious target for investigation in IBD models as a consequence of its ubiquitous expression in inflammatory cells. Studies investigating the efficacy of p38 inhibitors in animal models of IBD and human biopsies from IBD patients indicated that p38 could be a target for the treatment of IBD (Hove, T. ten et al., *Gut*, 2002, 50:507-512, Docena, G. et al., *J. Trans. Immunol.* 2010, 162:108-115). However, these findings are not completely consistent with other groups reporting no effect with p38 inhibitors (Malamut G. et al., *Dig. Dis. Sci,* 2006, 51:1443-1453). A clinical study in Crohn's patients using the p38 alpha inhibitor BIRB796 demonstrated potential clinical benefit with an improvement in C-reactive protein levels. However this improvement was transient, returning to baseline by week 8 (Schreiber, S. et al., *Clin. Gastro. Hepatology,* 2006, 4:325-334). A small clinical study investigating the efficacy of CNI-1493, a p38 and Jnk inhibitor, in patients with severe Crohn's disease showed significant improvement in clinical score over 8 weeks (Hommes, D. et al. *Gastroenterology.* 2002 122:7-14).

T cells are known to play a key role in mediating inflammation of the gastrointestinal tract. Pioneering work by Powrie and colleagues demonstrated that transfer of naive CD4+ cells into severely compromised immunodeficient (SCID) animals results in the development of colitis which is dependent on the presence of commensal bacteria (Powrie F. et al. *Int Immunol.* 1993 5:1461-71). Furthermore, investigation of mucosal membranes from IBD patients showed an upregulation of CD4+ cells which were either Th1 (IFNγ/IL-2) or Th2 (IL5/TGFβ) biased, depending on whether the patient had Crohn's disease or ulcerative colitis (Fuss I J. et al. *J. Immunol.* 1996, 157:1261-70). Similarly, T cells are known to play a key role in inflammatory disorders of the eye with several studies reporting increased levels of T cell associated cytokines (IL-17 and IL-23) in sera of Bechets patients (Chi W. et al. *Invest. Ophthalmol. Vis. Sci.* 2008, 49:3058-64). In support of these observations, Direskeneli and colleagues demonstrated that Bechets patients have increased Th17 cells and decreased Treg cells in their peripheral blood (Direskeneli H. et al. J Allergy Clin Immunol. 2011 128:665-6).

One approach to inhibit T cell activation is to target kinases which are involved in activation of the T cell receptor signalling complex. Syk and Src family kinases are known to play a key role in this pathway, where Src family kinases, Fyn and Lck, are the first signalling molecules to be activated downstream of the T cell receptor (Barber E K. et al. *PNAS* 1989, 86:3277-81). They initiate the tyrosine phosphorylation of the T cell receptor leading to the recruitment of the Syk family kinase, ZAP-70. Animal studies have shown that ZAP-70 knockout results in a SCID phenotype (Chan A C. et al. *Science.* 1994, 10; 264(5165):1599-601).

A clinical trial in rheumatoid arthritis patients with the Syk inhibitor Fostamatinib demonstrated the potential of Syk as an anti-inflammatory target, with patients showing improved clinical outcome and reduced serum levels of IL-6 and MMP-3 (Weinblatt M E. et al. *Arthritis Rheum.* 2008 58:3309-18). Syk kinase is widely expressed in cells of the hematopoietic system, most notably in B cells and mature T cells. Through interaction with immunoreceptor tyrosine-based activation motifs (ITAM), it plays an important role in regulating T cell and B cell expansion as well as mediating immune-receptor signalling in inflammatory cells. Syk activation leads to IL-6 and MMP release-inflammatory mediators commonly found upregulated in inflammatory disorders, including IBD and rheumatoid arthritis (Wang Y D. et al *World J Gastroenterol* 2007; 13: 5926-5932, Litinsky I et al. *Cytokine.* 2006 January 33:106-10).

In addition to playing key roles in cell signalling events which control the activity of pro-inflammatory pathways, kinase enzymes are now also recognised to regulate the activity of a range of cellular functions, including the maintenance of DNA integrity (Shilo, Y. *Nature Reviews Cancer,* 2003, 3: 155-168) and co-ordination of the complex processes of cell division. Indeed, certain kinase inhibitors (the so-called "Olaharski kinases") have been found to alter the frequency of micronucleus formation in vitro (Olaharski, A. J. et al., *PLoS Comput. Biol.,* 2009, 5(7), e1000446; doi: 10.1371/journal.pcbi.1000446). Micronucleus formation is implicated in, or associated with, disruption of mitotic processes and is therefore undesirable. Inhibition of glycogen synthase kinase 3α (GSK3α) was found to be a particularly significant factor that increases the likelihood of a kinase inhibitor promoting micronucleus formation. Also, inhibition of the kinase GSK3β with RNAi has been reported to promote micronucleus formation (Tighe, A. et al., *BMC Cell Biology,* 2007, 8:34).

Whilst it may be possible to attenuate the adverse effects of inhibition of Olaharski kinases such as GSK3α by optimisation of the dose and/or by changing the route of administration of a molecule, it would be advantageous to identify further therapeutically useful molecules with low or negligible inhibition of Olaharski kinases, such as GSK 3α, and/or have low or negligible disruption of mitotic processes (e.g. as measured in a mitosis assay).

Various compounds, including urea derivatives, are disclosed as inhibiting one or more kinases. Examples of such compounds may be found in WO 99/23091, WO 00/041698, WO 00/043384, WO 00/055139, WO 01/36403, WO 01/04115, WO 02/083628, WO 02/083642, WO 02/092576, WO 02/096876, WO 2003/005999, WO 2003/068223, WO 2003/068228, WO 2003/072569, WO 2004/014870, WO 2004/113352, WO 2005/005396, WO 2005/018624, WO 2005/023761, WO 2005/044825, WO 2006/015775, WO 2006/043090, WO 2007/004749 and WO 2007/053394. Further examples may be found in articles published in:

Curr. Opin. Drug Devel. (2004, 7(5), 600-616);
J. Med. Chem. (2007, 50, 4016-4026; 2009, 52, 3881-3891; and 2010, 53, 5639-5655);
Bioorg. Med. Chem. Lett. (2007, 17, 354-357; 2008, 18, 3251-3255; 2009, 19, 2386-2391; and 2010, 20, 4819-4824);
Curr. Top. Med. Chem. (2008, 8, 1452-1467);
Bioorg. Med. Chem. (2010, 18, 5738-5748);
Eur. J. Pharmacol. (2010, 632, 93-102) and
J. Chem. Inf. Model. (2011, 51, 115-129).

Nevertheless, there remains a need to identify and develop new kinase inhibitors, specifically alternative p38 MAP kinase inhibitors that are suitable for the treatment of inflammation. There is particularly a need for such inhibitors that have improved therapeutic potential over currently available treatments or, in particular, that exhibit a superior therapeutic index (e.g. inhibitors that are at least equally efficacious and, in one or more respects, are less toxic at the relevant therapeutic dose than previous agents).

SUMMARY OF THE INVENTION

We have now discovered, surprisingly, that an aniline-substituted diarylurea inhibits one or more of p38 MAP kinase, Syk and Src family kinases and therefore possess good anti-inflammatory properties.

Thus, according to a first aspect of the invention, there is provided a compound of formula I, example, compounds of formula I that are isotopically enriched or labelled with one or more atoms such as deuterium or the like.

The compound of formula I may exhibit tautomerism. All tautomeric forms and mixtures thereof are included within the scope of the invention.

The compound of formula I has the name 3-((4-((4-(3-(5-(tert-butyl)-2-methoxy-3-(methylsulfonamido)phenyl)ureido)naphthalen-1-yl)oxy)pyrimidin-2-yl)amino)-5-ethynyl-N-(2-(2-(2-methoxyethoxy)ethoxy)ethyl)benzamide. However, it may also be called 3-[[4-[[4-[[5-tert-butyl-3-(methanesulfonamido)-2-methoxy-phenyl]carbamoylamino]-1-naphthyl]oxy]-pyrimidin-2-yl]amino]-5-ethynyl-N-[2-[2-(2-methoxyethoxy)ethoxy]ethyl]benzamide.

Thus, in one embodiment, the invention relates to 3-((4-((4-(3-(5-(tert-butyl)-2-methoxy-3-(methylsulfonamido)phenyl)ureido)naphthalen-1-yl)oxy)pyrimidin-2-yl)amino)-5-ethynyl-N-(2-(2-(2-methoxyethoxy)ethoxy)ethyl)benzamide.

I

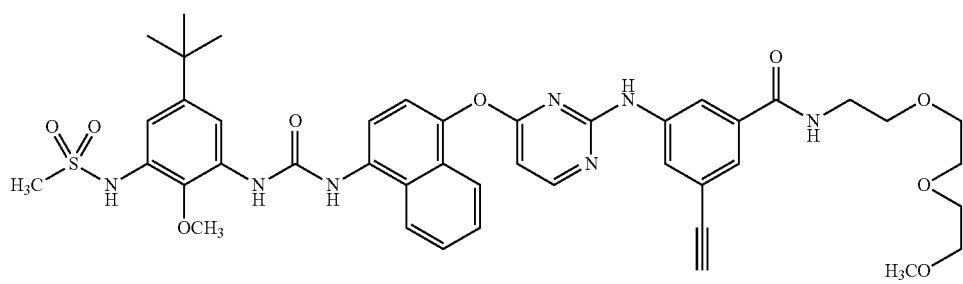

or a pharmaceutically acceptable salt thereof,
which compound may be referred to hereinafter as "the compound of the invention".

Pharmaceutically acceptable salts that may be mentioned include acid addition salts and base addition salts. Such salts may be formed by conventional means, for example by reaction of a free acid or a free base form of a compound of formula I with one or more equivalents of an appropriate acid or base, optionally in a solvent, or in a medium in which the salt is insoluble, followed by removal of said solvent, or said medium, using standard techniques (e.g. in vacuo, by freeze-drying or by filtration). Salts may also be prepared by exchanging a counter-ion of a compound of formula I in the form of a salt with another counter-ion, for example using a suitable ion exchange resin.

Examples of pharmaceutically acceptable salts include acid addition salts derived from mineral acids and organic acids, and salts derived from metals.

For the avoidance of doubt, the compound of formula I may contain the stated atoms in any of their natural or non-natural isotopic forms. In this respect, embodiments of the invention that may be mentioned include those in which:
(a) the compound of formula I is not isotopically enriched or labelled with respect to any atoms of the compound; and
(b) the compound of formula I is isotopically enriched or labelled with respect to one or more atoms of the compound.

References herein to an "isotopic derivative" relate to the second of these two embodiments. In particular embodiments of the invention, the compound of formula I is isotopically enriched or labelled (with respect to one or more atoms of the compound) with one or more stable isotopes. Thus, the compounds of the invention that may be mentioned include, for Examples of salts of the compound of formula I include all pharmaceutically acceptable salts, such as, without limitation, acid addition salts of strong mineral acids such as HCl and HBr salts and addition salts of strong organic acids such as methanesulfonic acid.

References herein to a compound of the invention (a compound of formula I) are intended to include references to the compound and to all pharmaceutically acceptable salts, solvates, isotopic derivatives and/or tautomers of said compound, unless the context specifically indicates otherwise. In this respect, solvates that may be mentioned include hydrates.

The compound of the invention (compound of formula I) is an inhibitor of p38 MAP kinases (especially of the alpha subtype), Syk kinase and Src family kinases, e.g., Src and Lck, and is therefore useful in medicine, in particular for the treatment of inflammatory diseases. Further aspects of the invention that may be mentioned therefore include the following.

(a) A pharmaceutical formulation comprising compound of formula I, as hereinbefore defined, or pharmaceutically acceptable salt thereof, in admixture with a pharmaceutically acceptable adjuvant, diluent or carrier.

(b) A combination product comprising
 (A) a compound of formula I, as hereinbefore defined, or pharmaceutically acceptable salt thereof, and
 (B) another therapeutic agent,
 wherein each of components (A) and (B) is formulated in admixture with a pharmaceutically-acceptable adjuvant, diluent or carrier.
 In this aspect of the invention, the combination product may be either a single (combination) pharmaceutical formulation or a kit-of-parts.

Thus, this aspect of the invention encompasses a pharmaceutical formulation including a compound of formula I, as hereinbefore defined, or pharmaceutically acceptable salt thereof, and another therapeutic agent, in admixture with a pharmaceutically acceptable adjuvant, diluent or carrier (which formulation is hereinafter referred to as a "combined preparation").

It also encompasses a kit of parts comprising components:
(i) a pharmaceutical formulation including a compound of formula I, as hereinbefore defined, or pharmaceutically acceptable salt thereof, in admixture with a pharmaceutically acceptable adjuvant, diluent or carrier; and
(ii) a pharmaceutical formulation including another therapeutic agent, in admixture with a pharmaceutically-acceptable adjuvant, diluent or carrier,
which components (i) and (ii) are each provided in a form that is suitable for administration in conjunction with the other.

Component (i) of the kit of parts is thus component (A) above in admixture with a pharmaceutically acceptable adjuvant, diluent or carrier. Similarly, component (ii) is component (B) above in admixture with a pharmaceutically acceptable adjuvant, diluent or carrier.

(c) A process for preparing the pharmaceutical formulation of aspect (a) above, said process comprising the step of admixing the compound of formula I, as hereinbefore defined, or pharmaceutically acceptable salt thereof, with a pharmaceutically acceptable adjuvant, diluent or carrier.

Embodiments of this aspect of the invention that may be mentioned include those in which the pharmaceutically acceptable adjuvant, diluent or carrier is a topically acceptable adjuvant, diluent or carrier (and/or wherein the process is for preparing a topical pharmaceutical formulation, i.e. a pharmaceutical formulation that is adapted for topical administration).

(d) A compound of formula I, as hereinbefore defined, or pharmaceutically acceptable salt thereof, for use in medicine (or for use as a medicament or as a pharmaceutical).

(e) A compound of formula I, as hereinbefore defined, or pharmaceutically acceptable salt thereof, or a pharmaceutical formulation or combination product, as defined in connection with aspect (a) or (b) of the invention, for use in the treatment or prevention of an inflammatory disease.

(f) The use of
a compound of formula I, as hereinbefore defined, or pharmaceutically acceptable salt thereof, or
a pharmaceutical formulation or combination product, as defined in connection with aspect (a) or (b) of the invention, for the preparation of a medicament for the treatment or prevention of an inflammatory disease.

(g) A method of treating or preventing an inflammatory disease, said method comprising administering to a subject an effective amount of
a compound of formula I, as hereinbefore defined, or pharmaceutically acceptable salt thereof, or
a pharmaceutical formulation or combination product, as defined in connection with aspect (a) or (b) of the invention.

(h) A method of sensitizing a subject to the anti-inflammatory effects of a corticosteroid, said method comprising administering to the subject an effective amount of
a compound of formula I, as hereinbefore defined, or pharmaceutically acceptable salt thereof, or
a pharmaceutical formulation or combination product, as defined in connection with aspect (a) or (b) of the invention.

Embodiments of this aspect of the invention that may be mentioned include those in which the subject is one who has become refractory to the anti-inflammatory effects of a corticosteroid.

DETAILED DESCRIPTION OF THE PREFERRED EMBODIMENT

Formulations

In relation to aspects (a) and (b) above, diluents and carriers that may be mentioned include those suitable for parenteral, oral, topical, mucosal and rectal administration.

The pharmaceutical formulations and combination products of aspects (a) and (b) above may be prepared e.g. for parenteral, subcutaneous, intramuscular, intravenous, intra-articular, intravitreous, periocular, retrobulbar, subconjunctival, sub-Tenon, topical ocular or peri-articular administration, particularly in the form of liquid solutions, emulsions or suspensions; for oral administration, particularly in the form of tablets or capsules, and especially involving technologies aimed at furnishing colon-targeted drug release (Patel, M. M. *Expert Opin. Drug Deliv.* 2011, 8 (10), 1247-1258); for topical e.g. pulmonary or intranasal administration, particularly in the form of powders, nasal drops or aerosols and transdermal administration; for topical ocular administration, particularly in the form of solutions, emulsions, suspensions, ointments, implants/inserts, gels, jellies or liposomal microparticle formulations (Ghate, D.; Edelhauser, H. F. *Expert Opin. Drug Deliv.* 2006, 3 (2), 275-287); for ocular administration, particularly in the form of biodegradable and non-biodegradable implants, liposomes and nanoparticles (Thrimawithana, T. R. et al. *Drug Discov. Today* 2011, 16 (5/6), 270-277); for mucosal administration e.g. to buccal, sublingual or vaginal mucosa, and for rectal administration e.g. in the form of a suppository or enema.

The pharmaceutical formulations and combination products of aspects (a) and (b) above may conveniently be administered in unit dosage form and may be prepared by any of the methods well-known in the pharmaceutical art, for example as described in Remington's Pharmaceutical Sciences, 17th ed., Mack Publishing Company, Easton, Pa., (1985). Formulations for parenteral administration may contain as excipients sterile water or saline, alkylene glycols such as propylene glycol, polyalkylene glycols such as polyethylene glycol, oils of vegetable origin, hydrogenated naphthalenes and the like. Formulations for nasal administration may be solid and may contain excipients, for example, lactose or dextran, or may be aqueous or oily solutions for use in the form of nasal drops or metered sprays. For buccal administration, typical excipients include sugars, calcium stearate, magnesium stearate, pregelatinated starch, and the like.

Pharmaceutical formulations and combination products suitable for oral administration may comprise one or more physiologically compatible carriers and/or excipients and may be in solid or liquid form. Tablets and capsules may be prepared with binding agents, for example, syrup, acacia, gelatin, sorbitol, tragacanth, or poly-vinylpyrollidone; fillers, such as lactose, sucrose, corn starch, calcium phosphate, sorbitol, or glycine; lubricants, such as magnesium stearate, talc, polyethylene glycol, or silica; and surfactants, such as sodium lauryl sulfate. Liquid compositions may contain conventional additives such as suspending agents, for example sorbitol syrup, methyl cellulose, sugar syrup, gelatin, carboxymethyl-cellulose, or edible fats; emulsifying agents such as lecithin, or acacia; vegetable oils such as almond oil, coconut oil, cod liver oil, or peanut oil; preservatives such as butylated hydroxyanisole (BHA) and butylated hydroxytoluene (BHT). Liquid compositions may be encapsulated in, for example, gelatin to provide a unit dosage form.

Solid oral dosage forms include tablets, two-piece hard shell capsules and soft elastic gelatin (SEG) capsules. Such two-piece hard shell capsules may be made from, for example, gelatin or hydroxylpropyl methylcellulose (HPMC).

A dry shell formulation typically comprises of about 40% to 60% w/w concentration of gelatin, about a 20% to 30% concentration of plasticizer (such as glycerin, sorbitol or propylene glycol) and about a 30% to 40% concentration of water. Other materials such as preservatives, dyes, opacifiers and flavours also may be present. The liquid fill material comprises a solid drug that has been dissolved, solubilized or dispersed (with suspending agents such as beeswax, hydrogenated castor oil or polyethylene glycol 4000) or a liquid drug in vehicles or combinations of vehicles such as mineral oil, vegetable oils, triglycerides, glycols, polyols and surface-active agents.

The compound of the invention may be administered topically (e.g. to the lung, eye or intestines). Thus, embodiments of aspects (a) and (b) above that may be mentioned include pharmaceutical formulations and combination products that are adapted for topical administration. Such formulations include those in which the excipients (including any adjuvant, diluent and/or carrier) are topically acceptable.

Topical administration to the lung may be achieved by use of an aerosol formulation. Aerosol formulations typically comprise the active ingredient suspended or dissolved in a suitable aerosol propellant, such as a chlorofluorocarbon (CFC) or a hydrofluorocarbon (HFC). Suitable CFC propellants include trichloromonofluoromethane (propellant 11), dichlorotetrafluoroethane (propellant 114), and dichlorodifluoromethane (propellant 12). Suitable HFC propellants include tetrafluoroethane (HFC-134a) and heptafluoropropane (HFC-227). The propellant typically comprises 40% to 99.5% e.g. 40% to 90% by weight of the total inhalation composition. The formulation may comprise excipients including co-solvents (e.g. ethanol) and surfactants (e.g. lecithin, sorbitan trioleate and the like). Other possible excipients include polyethylene glycol, polyvinylpyrrolidone, glycerine and the like. Aerosol formulations are packaged in canisters and a suitable dose is delivered by means of a metering valve (e.g. as supplied by Bespak, Valois or 3M or alternatively by Aptar, Coster or Vari).

Topical administration to the lung may also be achieved by use of a non-pressurised formulation such as an aqueous solution or suspension. This may be administered by means of a nebuliser e.g. one that can be hand-held and portable or for home or hospital use (i.e. non-portable). The formulation may comprise excipients such as water, buffers, tonicity adjusting agents, pH adjusting agents, surfactants and co-solvents. Suspension liquid and aerosol formulations (whether pressurised or unpressurised) will typically contain the compound of the invention in finely divided form, for example with a $D_{50}$ of 0.5-10 µm e.g. around 1-5 µm. Particle size distributions may be represented using $D_{10}$, $D_{50}$ and $D_{90}$ values. The $D_{50}$ median value of particle size distributions is defined as the particle size in microns that divides the distribution in half. The measurement derived from laser diffraction is more accurately described as a volume distribution, and consequently the $D_{50}$ value obtained using this procedure is more meaningfully referred to as a $Dv_{50}$ value (median for a volume distribution). As used herein Dv values refer to particle size distributions measured using laser diffraction. Similarly, $D_{10}$ and $D_{90}$ values, used in the context of laser diffraction, are taken to mean $Dv_{10}$ and $Dv_{90}$ values and refer to the particle size whereby 10% of the distribution lies below the $D_{10}$ value, and 90% of the distribution lies below the $D_{90}$ value, respectively.

Topical administration to the lung may also be achieved by use of a dry-powder formulation. A dry powder formulation will contain the compound of the disclosure in finely divided form, typically with a mass mean aerodynamic diameter (MMAD) of 1-10 µm or a $D_{50}$ of 0.5-10 µm e.g. around 1-5 µm. Powders of the compound of the invention in finely divided form may be prepared by a micronization process or similar size reduction process. Micronization may be performed using a jet mill such as those manufactured by Hosokawa Alpine. The resultant particle size distribution may be measured using laser diffraction (e.g. with a Malvern Mastersizer 2000S instrument). The formulation will typically contain a topically acceptable diluent such as lactose, glucose or mannitol (preferably lactose), usually of large particle size e.g. an MMAD of 50 µm or more, e.g. 100 µm or more or a $D_{50}$ of 40-150 µm. As used herein, the term "lactose" refers to a lactose-containing component, including α-lactose monohydrate, β-lactose monohydrate, α-lactose anhydrous, β-lactose anhydrous and amorphous lactose. Lactose components may be processed by micronization, sieving, milling, compression, agglomeration or spray drying. Commercially available forms of lactose in various forms are also encompassed, for example Lactohale® (inhalation grade lactose; DFE Pharma), InhaLac®70 (sieved lactose for dry powder inhaler; Meggle), Pharmatose®(DFE Pharma) and Respitose® (sieved inhalation grade lactose; DFE Pharma) products. In one embodiment, the lactose component is selected from the group consisting of α-lactose monohydrate, α-lactose anhydrous and amorphous lactose. Preferably, the lactose is α-lactose monohydrate.

Dry powder formulations may also contain other excipients such as sodium stearate, calcium stearate or magnesium stearate.

A dry powder formulation is typically delivered using a dry powder inhaler (DPI) device. Examples of dry powder delivery systems include SPINHALER, DISKHALER, TURBOHALER, DISKUS and CLICKHALER. Further examples of dry powder delivery systems include ECLIPSE, NEXT, ROTAHALER, HANDIHALER, AEROLISER, CYCLOHALER, BREEZHALER/NEOHALER, MONODOSE, FLOWCAPS, TWINCAPS, X-CAPS, TURBOSPIN, ELPENHALER, MIATHALER, TWISTHALER, NOVOLIZER, PRESSAIR, ELLIPTA, ORIEL dry powder inhaler, MICRODOSE, PULVINAL, EASYHALER, ULTRAHALER, TAIFUN, PULMOJET, OMNIHALER, GYROHALER, TAPER, CONIX, XCELOVAIR and PROHALER.

In one embodiment a compound of the present invention is provided in a micronized dry powder formulation, for example further comprising lactose of a suitable grade optionally together with magnesium stearate, filled into a single dose device such as AEROLISER or filled into a multi dose device such as DISKUS.

The compound of the present invention may also be administered rectally, for example in the form of suppositories or enemas, which include aqueous or oily solutions as well as suspensions and emulsions. Such compositions are prepared following standard procedures, well known by those skilled in the art. For example, suppositories can be prepared by mixing the active ingredient with a conventional suppository base such as cocoa butter or other glycerides, e.g., Suppocire. In this case, the drug is mixed with a suitable non-irritating excipient which is solid at ordinary temperatures but liquid at the rectal temperature and will therefore melt in the rectum to release the drug. Such materials are cocoa butter and polyethylene glycols.

Generally, for compositions intended to be administered topically to the eye in the form of eye drops or eye ointments, the total amount of the inhibitor will be about 0.0001 to less than 4.0% (w/w).

Preferably, for topical ocular administration, the compositions administered according to the present invention will be formulated as solutions, suspensions, emulsions and other dosage forms. Aqueous solutions are generally preferred, based on ease of formulation, as well as a patients ability to administer such compositions easily by means of instilling one to two drops of the solutions in the affected eyes. However, the compositions may also be suspensions, viscous or semi-viscous gels, or other types of solid or semi-solid compositions. Suspensions may be preferred for compounds that are sparingly soluble in water.

The compositions administered according to the present invention may also include various other ingredients, including, but not limited to, tonicity agents, buffers, surfactants, stabilizing polymer, preservatives, co-solvents and viscosity building agents. Preferred pharmaceutical compositions of the present invention include the inhibitor with a tonicity agent and a buffer. The pharmaceutical compositions of the present invention may further optionally include a surfactant and/or a palliative agent and/or a stabilizing polymer.

Various tonicity agents may be employed to adjust the tonicity of the composition, preferably to that of natural tears for ophthalmic compositions. For example, sodium chloride, potassium chloride, magnesium chloride, calcium chloride, simple sugars, such as dextrose, fructose, galactose, and/or simply polyols, such as the sugar alcohols mannitol, sorbitol, xylitol, lactitol, isomaltitol, maltitol, and hydrogenated starch hydrolysates may be added to the composition to approximate physiological tonicity. Such an amount of tonicity agent will vary, depending on the particular agent to be added. In general, however, the compositions will have a tonicity agent in an amount sufficient to cause the final composition to have an ophthalmically acceptable osmolality (generally about 150-450 mOsm, preferably 250-350 mOsm and most preferably at approximately 290 mOsm). In general, the tonicity agents of the invention will be present in the range of 2 to 4% w/w. Preferred tonicity agents of the invention include the simple sugars or the sugar alcohols, such as D-mannitol.

An appropriate buffer system (e.g., sodium phosphate, sodium acetate, sodium citrate, sodium borate or boric acid) may be added to the compositions to prevent pH drift under storage conditions. The particular concentration will vary, depending on the agent employed. Preferably however, the buffer will be chosen to maintain a target pH within the range of pH 5 to 8, and more preferably to a target pH of pH 5 to 7.

Surfactants may optionally be employed to deliver higher concentrations of inhibitor. The surfactants function to solubilise the inhibitor and stabilise colloid dispersion, such as micellar solution, microemulsion, emulsion and suspension. Examples of surfactants which may optionally be used include polysorbate, poloxamer, polyoxyl 40 stearate, polyoxyl castor oil, tyloxapol, triton, and sorbitan monolaurate. Preferred surfactants to be employed in the invention have a hydrophile/lipophile/balance "HLB" in the range of 12.4 to 13.2 and are acceptable for ophthalmic use, such as TritonX114 and tyloxapol.

Additional agents that may be added to the ophthalmic compositions of the present invention are demulcents which function as a stabilising polymer. The stabilizing polymer should be an ionic/charged example with precedence for topical ocular use, more specifically, a polymer that carries negative charge on its surface that can exhibit a zeta-potential of (−)10-50 mV for physical stability and capable of making a dispersion in water (i.e. water soluble). A preferred stabilising polymer of the invention would be polyelectrolyte, or polyelectrolytes if more than one, from the family of cross-linked polyacrylates, such as carbomers, polycarbophil and Pemulen®, specifically Carbomer 974p (polyacrylic acid), at 0.1-0.5% w/w.

Other compounds may also be added to the ophthalmic compositions of the present invention to increase the viscosity of the carrier. Examples of viscosity enhancing agents include, but are not limited to: polysaccharides, such as hyaluronic acid and its salts, chondroitin sulfate and its salts, dextrans, various polymers of the cellulose family, vinyl polymers and acrylic acid polymers.

Topical ophthalmic products are typically packaged in multidose form. Preservatives are thus required to prevent microbial contamination during use. Suitable preservatives include: benzalkonium chloride, chlorobutanol, benzododecinium bromide, methyl paraben, propyl paraben, phenylethyl alcohol, edentate disodium, sorbic acid, polyquaternium-1, or other agents known to those skilled in the art. Such preservatives are typically employed at a level of from 0.001 to 1.0% w/v. Unit dose compositions of the present invention will be sterile, but typically unpreserved. Such compositions, therefore, generally will not contain preservatives.

The medical practitioner, or other skilled person, will be able to determine a suitable dosage for the compound of the invention, and hence the amount of the compound of the invention that should be included in any particular pharmaceutical formulation (whether in unit dosage form or otherwise).

Embodiments of the invention that may be mentioned in connection with the combination products described at (b) above include those in which the other therapeutic agent is one or more therapeutic agents that are known by those skilled in the art to be suitable for treating inflammatory diseases (e.g. the specific diseases mentioned below).

For example, for the treatment of respiratory disorders (such as COPD or asthma), the other therapeutic agent is one or more agents selected from the list comprising:
  steroids (e.g. budesonide, beclomethasone dipropionate, fluticasone propionate, mometasone furoate, fluticasone furoate; a further example is ciclesonide);
  beta agonists, particularly beta2 agonists (e.g. terbutaline, salbutamol, salmeterol, formoterol; further examples are vilanterol, olodaterol, reproterol and fenoterol); and
  xanthines (e.g. theophylline).

For example, for the treatment of respiratory disorders (such as COPD or asthma), the other therapeutic agent is one or more agents selected from the list comprising:
  muscarinic antagonists (e.g. tiotropium, umeclidinium, glycopyrronium, aclidinium and daratropium, any of these, for example, as the bromide salt); and
  phosphodiesterase inhibitors.

Further, for the treatment of gastrointestinal disorders (such as Crohn's disease or ulcerative colitis), the other therapeutic agent may be, for example, one or more agents selected from the list comprising:
  5-aminosalicylic acid, or a prodrug thereof (such as sulfasalazine, olsalazine or bisalazide);
  corticosteroids (e.g. prednisolone, methylprednisolone, or budesonide);
  immunosuppressants (e.g. cyclosporin, tacrolimus, methotrexate, azathioprine or 6-mercaptopurine);

anti-TNFα antibodies (e.g., infliximab, adalimumab, certolizumab pegol or golimumab);
anti-IL12/IL23 antibodies (e.g., ustekinumab) or small molecule IL12/IL23 inhibitors (e.g., apilimod);
Anti-α4β7 antibodies (e.g., vedolizumab);
MAdCAM-1 blockers (e.g., PF-00547659);
antibodies against the cell adhesion molecule a4-integrin (e.g., natalizumab);
antibodies against the IL2 receptor α subunit (e.g., daclizumab or basiliximab);
JAK3 inhibitors (e.g., tofacitinib or R348);
Syk inhibitors and prodrugs thereof (e.g., fostamatinib and R-406);
Phosphodiesterase-4 inhibitors (e.g., tetomilast);
HMPL-004;
probiotics;
Dersalazine;
semapimod/CPSI-2364; and
protein kinase C inhibitors (e.g. AEB-071).

For the treatment of eye disorders (such as uveitis and keratoconjunctivitis sicca (dry eye)), the other therapeutic agent may be, for example, one or more agents selected from the list comprising:
corticosteroids (e.g. dexamethasone, prednisolone, triamcinolone acetonide, difluprednate or fluocinolone acetonide);
glucocorticoid agonists (e.g., mapracorat);
immunosuppressants (e.g. cyclosporin, voclosporin, azathioprine, methotrexate, mycophenolate mofetil or tacrolimus);
anti-TNFα antibodies (e.g., infliximab, adalimumab, certolizumab pegol, ESBA-105 or golimumab);
anti-IL-17A antibodies (e.g., secukinumab);
mTOR inhibitors (e.g., sirolimus);
VGX-1027;
adenosine A3 receptor agonists (e.g., CF-101);
lifitegrast;
JAK3 inhibitors (e.g., tofacitinib or R348); and
protein kinase C inhibitors (e.g. AEB-071).

In particular embodiments, for the treatment of eye disorders (such as uveitis and keratoconjunctivitis sicca (dry eye)), the other therapeutic agent may be, for example, one or more agents selected from the list comprising:
corticosteroids (e.g. dexamethasone, prednisolone, triamcinolone acetonide, difluprednate or fluocinolone acetonide);
immunosuppressants (e.g. cyclosporin, voclosporin, azathioprine, methotrexate, mycophenolate mofetil or tacrolimus);
anti-TNFα antibodies (e.g., infliximab, adalimumab, certolizumab pegol, ESBA-105 or golimumab);
anti-IL-17A antibodies (e.g., secukinumab);
mTOR inhibitors (e.g., sirolimus);
VGX-1027;
JAK3 inhibitors (e.g., tofacitinib or R348); and
protein kinase C inhibitors (e.g. AEB-071).

Medical Uses

The compound of the invention may be used as a monotherapy for inflammatory diseases, or in combination therapies for such diseases.

Thus, embodiments of aspects (e) to (g) above that may be mentioned include those in which the compound of formula I (or pharmaceutically acceptable salt thereof) is the sole pharmacologically active ingredient utilised in the treatment.

However, in other embodiments of aspects (e) to (g) above, the compound of formula I (or pharmaceutically acceptable salt thereof) is administered to a subject who is also administered one or more other therapeutic agents (e.g. wherein the one or more other therapeutic agents are as defined above in connection with combination products).

When used herein, the term "inflammatory disease" specifically includes references to any one or more of the following:
(i) lung diseases or disorders having an inflammatory component, such as cystic fibrosis, pulmonary hypertension, lung sarcoidosis, idiopathic pulmonary fibrosis or, particularly, COPD (including chronic bronchitis and emphysema), asthma or paediatric asthma;
(ii) skin diseases or disorders having an inflammatory component, such as atopic dermatitis, allergic dermatitis, contact dermatitis or psoriasis;
(iii) nasal diseases or disorders having an inflammatory component, such as allergic rhinitis, rhinitis or sinusitis;
(iv) eye diseases or disorders having an inflammatory component, such as conjunctivitis, allergic conjunctivitis, glaucoma, diabetic retinopathy, macular oedema (including diabetic macular oedema), central retinal vein occlusion (CRVO), dry and/or wet age related macular degeneration (AMD), post-operative cataract inflammation, or, particularly, keratoconjunctivitis sicca (dry eye), uveitis (including posterior, anterior and pan uveitis), corneal graft and limbal cell transplant rejection; and
(v) gastrointestinal diseases or disorders having an inflammatory component, such as gluten sensitive enteropathy (coeliac disease), eosinophilic esophagitis, intestinal graft versus host disease or, particularly, Crohn's disease or ulcerative colitis.

References herein to diseases having an inflammatory component include references to diseases that involve inflammation, whether or not there are other (non-inflammatory) symptoms or consequences of the disease.

According to a further aspect of the invention there is provided a process for the preparation of a compound of formula I which process comprises:
(a) reaction of a compound of formula II,

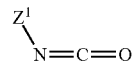

with a compound of formula III,

wherein one of $Z^1$ and $Z^2$ is a structural fragment of formula IV

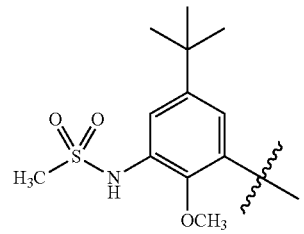

and the other of $Z^1$ and $Z^2$ is a structural fragment of formula V

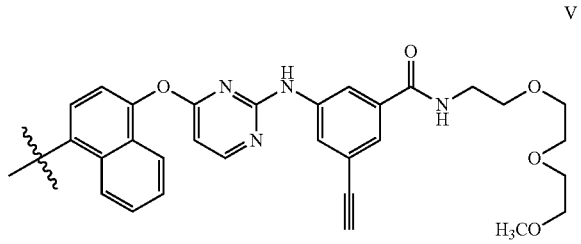 [SMILES: *c1ccc(Oc2ccnc(Nc3cc(C#C)cc(C(=O)NCCOCCOCCOC)c3)n2)c2ccccc12]

for example under conditions known to those skilled in the art, for example at a temperature from ambient (e.g. 15 to 30° C.) to about 110° C. in the presence of a suitable organic solvent (e.g. a polar aprotic solvent such as DMF, THF, 1,4-dioxane, or mixtures thereof);
(b) reaction of a compound of formula IIa,

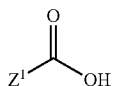

wherein $Z^1$ is as defined above, with a suitable azide-forming agent (i.e. a suitable source of a leaving group and activated azide ion, such as diphenyl phosphorazidate; see, for example, *Tetrahedron* 1974, 30, 2151-2157) under conditions known to those skilled in the art, such as at sub-ambient to ambient temperature (e.g. from an initial temperature of about −5 to 5° C. to ambient temperature post-reaction) in the presence of an amine base (e.g. triethylamine or a sterically hindered base such as N,N-diisopropylethylamine) and a suitable organic solvent (e.g. a polar aprotic solvent such as DMF, THF, 1,4-dioxane, or mixtures thereof), which reaction is followed, without isolation, by thermal rearrangement (e.g. under heating) of the intermediate acyl azide (of formula $Z^1$—C(O)—$N_3$) e.g. at ambient temperature (such as from 15 to 30° C.) to provide, in situ, a compound of formula II, which compound is then reacted with a compound of formula III, as defined above, to provide the compound of formula I;
(c) reaction of a compound of formula IIb,

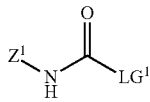

wherein $LG^1$ represents a suitable leaving group (e.g. imidazolyl, chloro, or aryloxy, such as phenoxy) and $Z^1$ is as defined above, with a compound of formula III, as defined above, for example under conditions known to those skilled in the art, such as at ambient temperature (e.g. from ambient to 80° C., such as at about 60° C.), optionally in the presence of an amine base (e.g. triethylamine or a sterically hindered base like N,N-diisopropylethylamine) and a suitable organic solvent (e.g. an aprotic solvent, such as dichloromethane or an ester such as isopropyl acetate);
(d) reaction of a compound of formula VI,

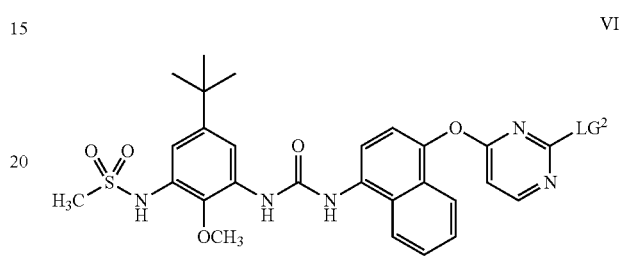

wherein $LG^2$ represents a suitable leaving group (e.g. a halo group such as chloro or bromo), with a compound of formula VII,

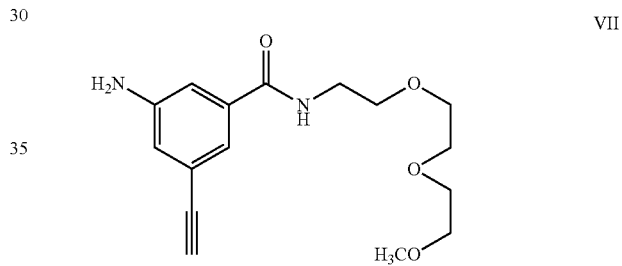

for example under conditions known to those skilled in the art (e.g. as described in *J. Am. Chem. Soc.* 2011, 133, 15686-15696), such as at elevated temperature (e.g. from 50 to 110° C.) in the presence of a suitable organic solvent (e.g. a polar aprotic solvent such as DMF, THF, 1,4-dioxane, or mixtures thereof) and, optionally, an acidic catalyst (e.g. a sulfonic acid such as para-toluenesulfonic acid) or through a Buchwald coupling (Surry, D. S.; Buchwald, S. L. *Chem. Sci.* 2011, 2, 27-50) involving a palladium catalyst and an appropriate ligand, e.g., BrettPhos; or (e) reaction of a compound of formula VIIIa,

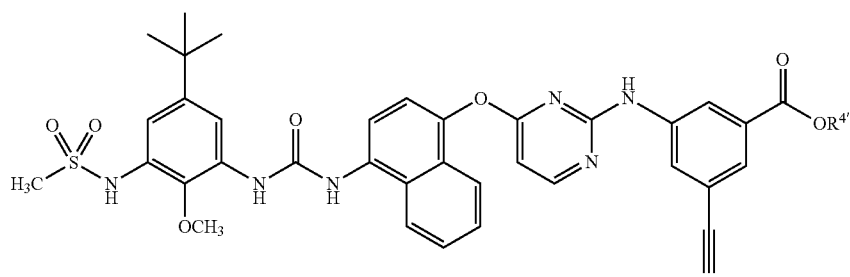

wherein R[4'] represents H or a $C_{1-3}$ alkyl group (e.g. methyl), with a compound of formula VIIb, $$H_2N-[CH_2CH_2-O]_2-CH_2CH_2-OCH_3 \quad \text{VIIb}$$

for example under conditions known to those skilled in the art, such as (i) when R[4'] represents a $C_{1-3}$ alkyl group, reaction at ambient temperature in the presence of a suitable Lewis acidic catalyst (e.g. a trialkylaluminium reagent such as trimethylaluminium) and an aprotic organic solvent (e.g. THF), (ii) when R[4'] represents H, reaction in the presence of a tertiary amine base (e.g. a trialkylamine such as triethylamine or diisopropylethylamine or a cyclic amine such as N-methylpyrrolidine or N-methylmorpholine), an amide (peptide) coupling reagent (e.g. T3P, HATU, CDI, BOP, PyBOP, HOAt, HOBt or a carbodiimide such as DCC or diisopropylcarbodiimide) and an aprotic organic solvent (e.g. a chlorinated solvent such as DCM, an ester such as ethyl acetate, an amide of dimethylamine such as DMF, or a mixture of any such solvents) or (iii) prior to reaction with the compound of formula VIIb, conversion of the compound of formula VIIIa to a corresponding compound in which OR[4'] is replaced by halo (e.g. chloro, which compound may, for example, be prepared by reaction of a compound of formula VIIIa in which R[4'] represents H with a halogenating agent such as thionyl chloride, for example at elevated temperature, such as from 50 to 70° C.), followed by reaction of the resulting acid halide with the compound of formula VIIb, which reaction may, for example, be carried out in the presence of an aprotic organic solvent (e.g. a chlorinated solvent such as DCM).

Compounds of formula II may be prepared according to or by analogy with methods known to those skilled in the art, for example by reaction of a compound of formula IIa, as defined above, with an azide-forming agent, followed by rearrangement of the intermediate acyl azide (as described at (b) above; see, for example, *Tetrahedron* 1974, 30, 2151-2157).

Compounds of formula IIb may be prepared reaction of a compound of formula VIII,

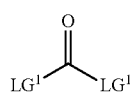

VIII wherein LG[1] is as hereinbefore defined, with a compound of formula IX,

IX wherein Z[1] is as hereinbefore defined, for example under conditions known to those skilled in the art.

Amines of formula IX may be prepared from carboxylic acids of formula IIa through the route described in (b) above, where the intermediate isocyanate II is hydrolysed with water to give a carbamic acid that loses carbon dioxide to furnish IX. By the same token, the intermediate isocyanate II can be reacted with an alcohol, such as t-butanol, to generate a protected version of IX.

Compounds of formula III in which Z[2] represents a structural fragment of formula V, or compounds of formula IX in which Z[1] represents a structural fragment of formula V, may be synthesised employing the route outlined in Scheme 1 (see, for example: WO 2003/072569; and WO 2008/046216), wherein LG[3] and LG[4] represent leaving groups, e.g., halogen or methanesulfonyl, and FG represents a real or latent $NH_2$ group, i.e., a group that is readily transformed into an $NH_2$ group, such as nitro or a protected variant NH—PG[2], where PG[2] is a typical protecting group (see, for example: Greene, T. W.; Wuts, P. G. M. *Protective Groups in Organic Synthesis*; Wiley, 4th revised edition, 2006; ISBN-10:0471697540), e.g., a carbamate ester or carboxamide. The sequence starts with the base-mediated $S_NAr$ displacement of LG[3] in XI by the aroxides formed when X is treated with base to generate ethers XII. The remaining halogen or methanesulfonyl substituent (LG[4]) of the ether XII is then displaced i) by an amine of formula VII in a second $S_NAr$ reaction or (ii) via a Buchwald coupling (see, for example, WO 2009/017838) with an amine of formula VII to furnish the desired compound (when FG is $NH_2$), or XIII (when FG is nitro or NH—PG[2]). When FG is nitro in XIII, the $NH_2$ group may be revealed by a reduction reaction, typically done through hydrogenation employing a suitable catalyst, e.g., palladium on carbon, or employing dissolving metal conditions, such as with iron in glacial acetic acid. Alternatively, when FG is a protecting group, the $NH_2$ group may be revealed by a deprotection reaction. Although only depicted as taking place in the final step of the sequence, it should be noted that the unmasking of the latent $NH_2$ group represented by FG can take place at any stage in the synthetic route shown in Scheme 1.

Scheme 1

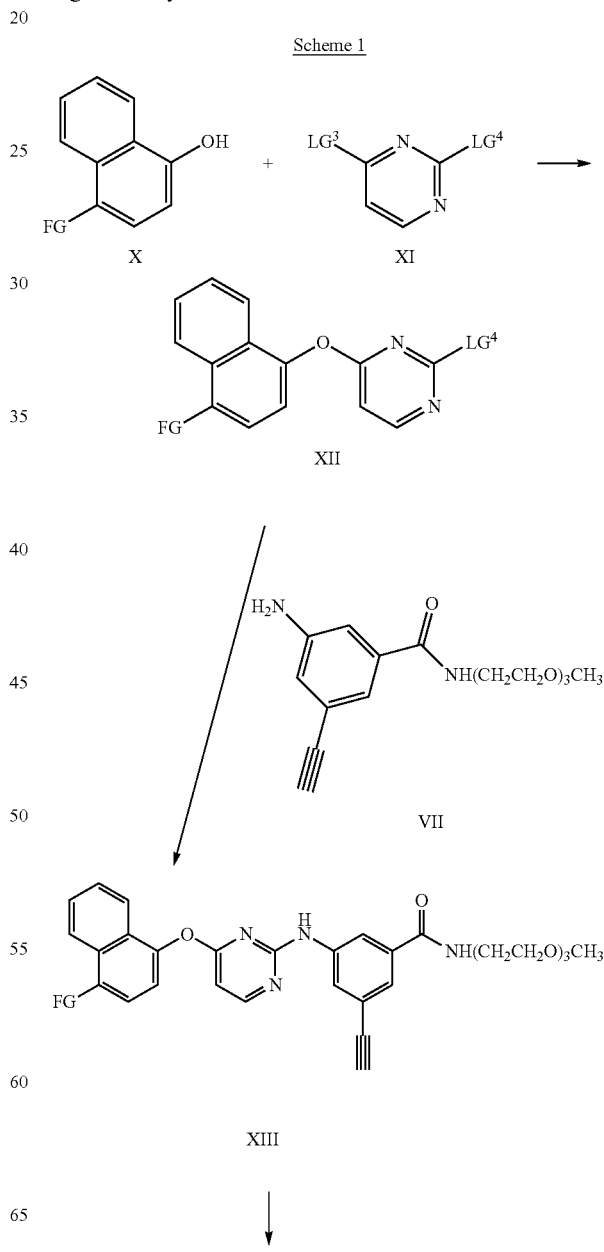

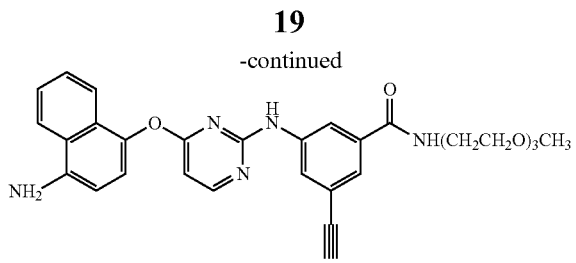

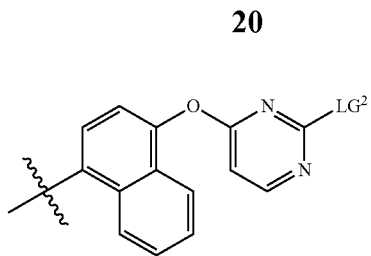

In a similar manner, amines of formula IX in which $Z^1$ represents a structural fragment of formula IV may be synthesised by conversion of a latent to a real $NH_2$ group in a compound of formula XIIIa, XIIIa

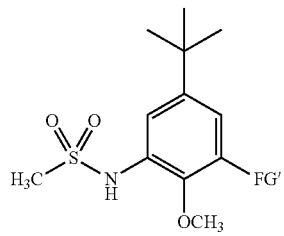

wherein FG' is as defined for FG above, except that it does not represent $NH_2$.

Compounds of formula III in which $Z^2$ represents a structural fragment of formula V, or compounds of formula IX in which $Z^1$ represents a structural fragment of formula V, may be prepared by analogy with processes described herein for preparing the compound of formula I (see process (e) above) and other compounds of formula III (see, for example, Scheme 1 above), for example by reaction of a compound of XIIIb XIIIb

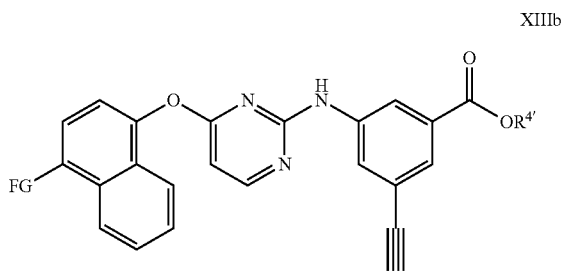

wherein FG and $R^{4'}$ are as hereinbefore defined, with a compound of formula VIIb, as hereinbefore defined, under conditions known to those skilled in the art (for example the peptide coupling conditions described in respect of process (e) above), followed by conversion (if necessary) of FG to $NH_2$, for example as described above in connection with Scheme 1.

Compounds of formula VI may be synthesised by analogy with the compound of formula I (see, for example, alternative processes (a) to (c) above). For example, compounds of formula VI can be prepared by reaction of a compound of formula IIx with a compound of formula IIIx, wherein the compounds of formulae IIx and IIIx take the same definitions as the compounds of formulae II and III, with the exception that one of $Z^1$ and $Z^2$ represents a structural fragment of formula IV, as hereinbefore defined, and the other of $Z^1$ and $Z^2$ represents a structural fragment of formula Va, Va The compound of formula VII may be prepared according to or by analogy with procedures known to those skilled in the art, for example by reaction of a compound of formula XIV,

XIV

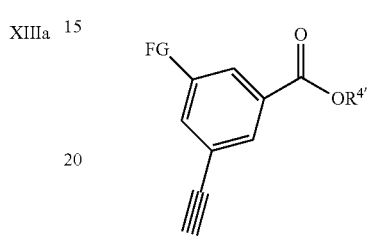

wherein FG is as hereinbefore defined, with a compound of formula VIIb, as hereinbefore defined, under conditions known to those skilled in the art (for example the peptide coupling conditions described in respect of process (e) above), followed by when FG represents $NH—PG^2$, removal of the $PG^2$ protecting group or, when FG represents $NO_2$, reduction of $NO_2$ to $NH_2$.

It will be understood by persons skilled in the art that compounds represented by formulae II, IIx and IIb are generally reactive intermediates. These intermediates may be formed in situ and reacted directly, without isolation, with compounds of formula III to provide the compound of formula I. Furthermore, it will be understood by those skilled in the art that the use of appropriate protective groups may be required during the processes described above for any of the groups $Z^1$ and $Z^2$ which possess chemically-sensitive functional groups, for example, a hydroxyl group or an amino function.

Many of the compounds illustrated in the Schemes are either commercially available, or can be obtained using the cited procedures, or can be readily prepared by conventional methods by those skilled in the art. See for example Regan, J. et al.; *J. Med. Chem.* 2003, 46, 4676-4686, WO 2000/043384, WO 2007/053346, WO 2007/087448, WO 2007/089512, WO 2009/117080 and WO 2014/027209.

A particular embodiment of the invention relates to a process for preparing the compound of formula I, which process comprises reaction of a compound of formula XV

XV

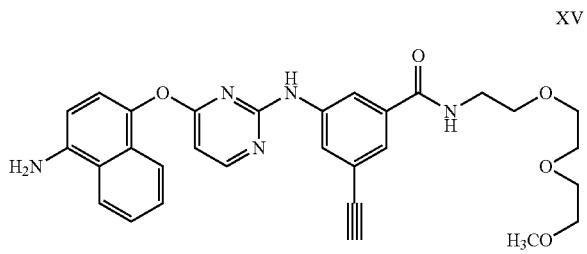 [SMILES: CCc1cc(Nc2nccc(Oc3ccc(N)c4ccccc34)n2)cc(C(=O)NCCOCCOCCOC)c1]

with a compound of formula XVI,

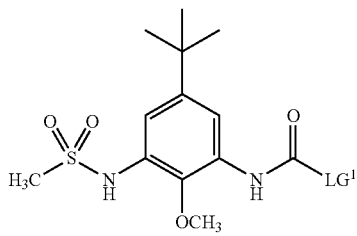

XVI wherein LG¹ is as hereinbefore defined (e.g. phenoxy), for example under conditions known to those skilled in the art, such as at elevated temperature (e.g. from 40 to 80° C., such as at about 60° C.), in the presence of an amine base (e.g. triethylamine) and an aprotic organic solvent (e.g. an ester such as isopropyl acetate).

The compound of formula XV may be prepared by deprotection of a corresponding compound of formula XVa, XVa

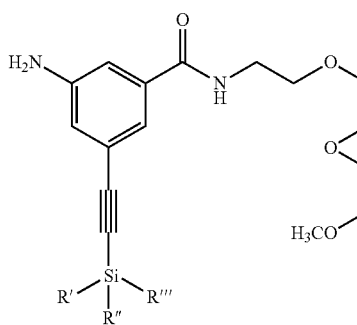

wherein $PG^2$ is as hereinbefore defined (e.g. $PG^2$ is tert-butoxycarbonyl), for example under conditions known to those skilled in the art, such as when $PG^2$ represents tert-butoxycarbonyl, reaction with a strong acid (e.g. an alkyl or arylsulfonic acid (e.g. p-toluenesulfonic acid and/or, particularly, trifluoroacetic acid) in the presence of an aprotic organic solvent (e.g. a chlorinated solvent such as DCM).

The compound of formula XVa may be prepared by reaction of a compound of formula VII, as hereinbefore defined, with a compound of formula XII (e.g. a compound of formula XII in which LG⁴ represents chloro), as hereinbefore defined but in which FG represents NH-PG² (e.g. NH—C(O)O—C(CH₃)₃), for example under conditions known to those skilled in the art, such as at elevated temperature (e.g. from 40 to 80° C., such as between 60 and 70° C.), in the presence of an aprotic solvent (e.g. THF) and, optionally, an acid catalyst (e.g. a sulfonic acid, such as para-toluenesulfonic acid).

The compound of formula VII may be prepared by methods such as those described above. For example, the compound of formula VII may be prepared by deprotection of a compound of formula VII(P),

VII(P)

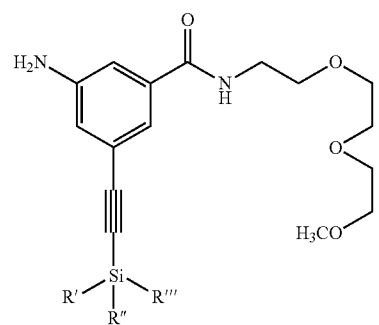

wherein R', R" and R'" independently represent $C_{1-4}$ alkyl (e.g. R', R" and R'" all represent isopropyl), for example under conditions known to those skilled in the art, such as reaction at ambient temperature in a polar, aprotic solvent (e.g. acetonitrile) with a source of fluoride ion, such as TBAF or caesium fluoride.

The compound of formula VII(P) may be prepared by coupling (e.g. Sonogashira coupling; see *Chem. Soc. Rev.* 2011, 40, 5084-5121) of a compound of formula XVII,

XVII

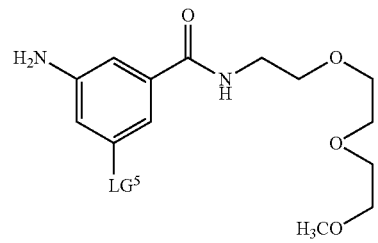

wherein LG⁵ represents halo, such as bromo, with a compound of formula XVIII,

XVIII

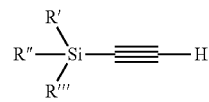

wherein R', R" and R'" are as hereinbefore defined, for example under conditions known to those skilled in the art, such as reaction at elevated temperature (e.g. 50 to 80° C. or, particularly, 60 to 70° C.) in the presence of CuI and a Pd(0) catalyst (e.g. Pd(PPh₃)₄) and a reaction-inert organic solvent, such as THF.

The compound of formula XVII may be prepared by reduction of a compound of formula XIX,

XIX

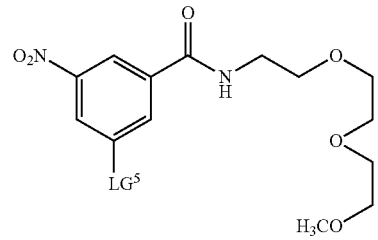

wherein LG⁵ is as hereinbefore defined, for example under conditions known to those skilled in the art, such as at elevated temperature (e.g. from about 50 to 70° C.) under a hydrogen atmosphere (e.g. under H₂ at a pressure of about 3 MPa) in the presence of a suitable catalyst (e.g. Pt/C), a reaction-inert solvent (e.g. THF) and an acid (e.g. acetic acid) or alternatively with iron in an acidic media (e.g. hydrochloric acid) in water and ethanol.

The compound of formula XIX may be prepared by reaction of a compound of formula XX,

XX

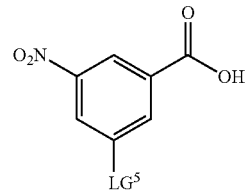

wherein LG⁵ is as hereinbefore defined, with a halogenating agent (e.g. thionyl chloride, for example at from 60 to 70° C.), followed by reaction of the intermediate acid halide with the compound of formula VIIb, as hereinbefore defined, for example under conditions known to those skilled in the art, such as at 25° C. or below in the presence of an aprotic organic solvent (e.g. DCM) and a base, e.g., triethylamine, DIPEA or NaHCO₃. Alternatively, this transformation may be effected by condensation in the presence of a tertiary amine base (e.g. a trialkylamine, such as triethylamine or DIPEA, or a cyclic amine, such as N-methylpyrrolidine or N-methylmorpholine), an amide (peptide) coupling reagent (e.g. T3P, HATU, CDI, BOP, PyBOP, HOAt, HOBt or a carbodiimide such as DCC or diisopropylcarbodiimide) and an aprotic organic solvent (e.g. a chlorinated solvent such as DCM, an ester such as ethyl acetate, an amide of dimethylamine such as DMF, or a mixture of any such solvents).

The compound of formula XVI may be prepared by reaction of a compound of formula XXI (US2003/0065034),

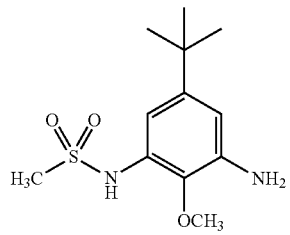

XXI with a compound of formula XXII,

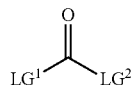

XXII wherein LG¹ and LG² represent leaving groups (e.g. LG¹ represents phenoxy and LG² represents halo, such as chloro), for example under conditions known to those skilled in the art, such as at below about 20° C. in the presence of a base (e.g. NaHCO₃) and a reaction-inert organic solvent (e.g. THF, DCM or, particularly, a mixture thereof).

The compound of formula XXI may be prepared by reduction of a compound of formula XXIII,

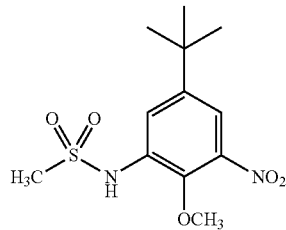

XXIII for example under conditions known to those skilled in the art, such as under a hydrogen atmosphere (e.g. under H₂ at a pressure of about 0.3 to 0.4 MPa) in the presence of a suitable catalyst (e.g. Pd/C) and a solvent (e.g. methanol).

The compound of formula XXI may be prepared by reaction of a compound of formula XXIV,

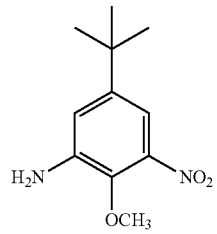

XXIV with methanesulfonyl chloride, for example under conditions known to those skilled in the art, such as at between 25 and 40° C. in the presence of a base (e.g. pyridine) and a reaction-inert organic solvent (e.g. toluene).

The compound of formula XXIV may be prepared by partial reduction of a compound of formula XXV,

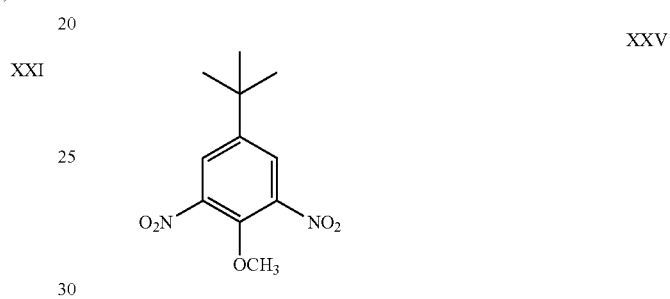

XXV for example under conditions known to those skilled in the art, such as at elevated temperature (e.g. from 70 to 80° C.) in the presence of a hydrogen source (e.g. 4-methyl-1-cyclohexene), a suitable catalyst (e.g. Pd/C) and a solvent (e.g. an alcohol such as methanol, ethanol or a mixture thereof, such as industrial methylated spirit).

In particular embodiments, the invention relates to a process for preparing a compound of formula I, said process comprising:
(a) a process as described herein for preparing a compound of formula XV; and/or
(b) a process as described herein for preparing a compound of formula XVI.

In connection with these embodiments of the invention, the process for preparing a compound of formula I may comprise a process as described herein for preparing any one or more of the compounds of formulae XVa, VII(P), VII, XVII, XIX, XXI, XXIII and XXIV.

Novel intermediates as described herein form an aspect of the invention. In this respect, a further aspect of the invention relates to a compound of formula XVI as hereinbefore defined (e.g. a compound of formula XVI in which LG¹ represents phenoxy).

The aspects of the invention described herein (e.g. the above-mentioned compounds, combinations, methods and uses) may have the advantage that, in the treatment of the conditions described herein, they may be more convenient for the physician and/or patient than, be more efficacious than, be less toxic than, have better selectivity over, have a broader range of activity than, be more potent than, produce fewer side effects than, have a better pharmacokinetic and/or pharmacodynamic profile than, have more suitable solid state morphology than, have better long term stability than, or may have other useful pharmacological properties over, similar compounds, combinations, methods (treatments) or uses known in the prior art for use in the treatment of those conditions or otherwise.

The compound of the invention may additionally (or alternatively):

exhibit a long duration of action and/or persistence of action (e.g. in comparison to other previously disclosed p38 MAP kinase inhibitors such as, for example, BIRB796);

not strongly inhibit GSK3α;

target a smaller portion of the kinome, i.e., with improved selectivity, as illustrated by lowered KinomeScan Selectivity Scores;

maintain a relatively high local drug concentration between doses (e.g. a high local concentration relative to other previously disclosed p38 MAP kinase inhibitors such as, for example, BIRB796);

exhibit properties that are particularly suited to topical/local administration (e.g. following topical/local administration, the generation of high target tissue concentrations, but low plasma concentrations, of the compound of formula (I) and/or rapid clearance of the compound of formula (I) from plasma, for example as a result of high renal or hepatic extraction);

exhibit little or no β-catenin induction and/or inhibition of mitosis in cells;

not produce increases in binucleated cells containing micronuclei in the human lymphocyte in vitro micronucleus test;

exhibit little or no time-dependent inhibition of members of the cytochrome P450 superfamily;

show improved chemical stability in the presence of water (e.g. stability to hydrolysis in aqueous mixtures at elevated temperatures) compared to previously disclosed p38 MAP kinase inhibitors such as, for example, BIRB796;

following administration to a patient, give rise to metabolites associated with little or no safety (e.g. toxicity) concerns;

exhibit good solubility and/or cellular permeability;

have a high degree of crystallinity; and/or exhibit little or no hygroscopicity in the solid state.

Experimental Methods

General Procedures

All starting materials and solvents were obtained either from commercial sources or prepared according to the literature citation. Unless otherwise stated, all reactions were stirred. Organic solutions were routinely dried over anhydrous magnesium sulfate. Microwave reactions were performed in a CEM Discover and Smithcreator microwave reactor, heating to a constant temperature using variable power microwave irradiation.

Normal phase column chromatography was routinely carried out on an automated flash chromatography system such as CombiFlash Companion or CombiFlash RF system using pre-packed silica (230-400 mesh, 40-63 µm) cartridges. SCX was purchased from Supelco and treated with 1M hydrochloric acid prior to use. Unless stated otherwise, the reaction mixture to be purified was first diluted with MeOH and made acidic with a few drops of AcOH.

This solution was loaded directly onto the SCX and washed with MeOH. The desired material was then eluted by washing with 1% $NH_3$ in MeOH.

Analytical Methods

Analytical HPLC was carried out using a Waters Xselect CSH C18, 2.5 µm, 4.6×30 mm column eluting with a gradient of 0.1% Formic Acid in MeCN in 0.1% aqueous Formic Acid or a Waters Xbridge BEH C18, 2.5 µm, 4.6×30 mm column eluting with a gradient of MeCN in aqueous 10 mM Ammonium Bicarbonate. UV spectra of the eluted peaks were measured using either a diode array or variable wavelength detector on an Agilent 1100 system.

Analytical LCMS was carried out using a Waters Xselect CSH C18, 2.5 µm, 4.6×30 mm column eluting with a gradient of 0.1% Formic Acid in MeCN in 0.1% aqueous Formic Acid or a Waters Xbridge BEH C18, 2.5 µm, 4.6×30 mm column eluting with a gradient of MeCN in aqueous 10 mM Ammonium Bicarbonate. UV and mass spectra of the eluted peaks were measured using a variable wavelength detector on either an Agilent 1200 or an Agilent Infinity 1260 LCMS with 6120 single quadrupole mass spectrometer with positive and negative ion electrospray.

Preparative HPLC was carried out using a Waters Xselect CSH C18, 5 µm, 19×50 mm column using either a gradient of either 0.1% Formic Acid in MeCN in 0.1% aqueous Formic Acid or a gradient of MeCN in aqueous 10 mM Ammonium Bicarbonate or employing a Waters Xbridge BEH C18, 5 µm, 19×50 mm column using a gradient of MeCN in aqueous 10 mM Ammonium Bicarbonate. Fractions were collected following detection by UV at a single wavelength measured by a variable wavelength detector on a Gilson 215 preparative HPLC or Varian PrepStar preparative HPLC or by mass and UV at a single wavelength measured by a ZQ single quadrupole mass spectrometer, with positive and negative ion electrospray, and a dual wavelength detector on a Waters Fraction Lynx LCMS.

$^1$H NMR Spectroscopy:

$^1$H NMR spectral data reported were acquired on a Bruker Avance III spectrometer at 400 MHz. Either the central peaks of chloroform-d, dimethylsulfoxide-$d_6$ or an internal standard of tetramethylsilane were used as references.

EXAMPLES

Example 1

3-((4-((4-(3-(5-(tert-Butyl)-2-methoxy-3-(methylsulfonamido)phenyl)ureido)naphthalen-1-yl)oxy)pyrimidin-2-yl)amino)-5-ethynyl-N-(2-(2-(2-methoxyethoxy)ethoxy)ethyl)benzamide (Compound I)

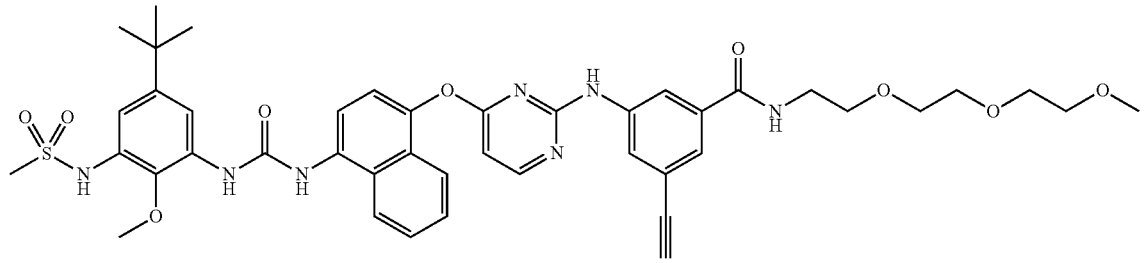

(i) 3-Bromo-N-(2-(2-(2-methoxyethoxy)ethoxy)ethyl)-5-nitrobenzamide

T3P, 50 wt % in EtOAc (25 mL, 42.0 mmol) was slowly added to a solution of 3-bromo-5-nitrobenzoic acid (7.05 g, 28.7 mmol), 2-(2-(2-methoxyethoxy)ethoxy)ethanamine (4 g, 24.25 mmol) and Et$_3$N (12 mL, 86 mmol) in EtOAc (50 mL) whilst immersed in an ice-bath. Once the addition was complete, the ice bath was removed and the reaction allowed to stir at rt for 2 h. The mixture was partitioned between sat. aq. NaHCO$_3$ solution (100 mL) and EtOAc (100 mL). The organic layer was washed with aq K$_2$CO$_3$ solution (10 g in 100 mL) and brine (100 mL), before being dried (MgSO$_4$), filtered and concentrated in vacuo to afford the sub-title compound (8.23 g) as a brown oil.

$^1$H NMR (400 MHz, DMSO-d6) δ 9.02 (t, 1H), 8.65-8.64 (m, 1H), 8.53 (t, 1H), 8.46 (t, 1H), 3.57-3.43 (m, 10H), 3.41-3.38 (m, 2H), 3.21 (s, 3H).

LCMS m/z 391/393 (M+H)$^+$ (ES$^+$); 389/391 (M−H)$^-$ (ES$^-$)

(ii) 3-Amino-5-bromo-N-(2-(2-(2-methoxyethoxy)ethyl)benzamide

Iron powder (5.90 g, 106 mmol) was added to a solution of the product from step (i) above (8.24 g, 20.43 mmol) and concentrated HCl (2 mL, 23.40 mmol) in EtOH (65 mL) and water (15 mL). The mixture was heat at 75° C. (block temperature) for 1 h. Then, the reaction was cooled to rt, before being diluted with water (30 mL), filtered and concentrated in vacuo. The residue was basified (NaHCO$_3$) then partitioned between EtOAc (350 mL) and water (275 mL). The organic layer was dried (MgSO$_4$), filtered and concentrated in vacuo to afford an orange oil that was purified by chromatography on silica gel (220 g column, 0-5% MeOH in DCM) to afford the sub-title compound (5.25 g) as an orange oil.

$^1$H NMR (400 MHz, DMSO-d6) δ: 8.36 (t, 1H), 7.07 (t, 1H), 7.00-6.99 (m, 1H), 6.84 (t, 1H), 5.57 (s, 2H), 3.52-3.48 (m, 8H), 3.42-3.39 (m, 2H), 3.35 (q, 2H), 3.22 (s, 3H).

LCMS m/z 361/363 (M+H)$^+$ (ES$^+$)

(iii) 3-Amino N-(2 (2 (2 methoxyethoxy)ethoxy)ethyl)-5-((triisopropyl)ethynyl)benzamide To a degassed solution of the product from step (ii) above (5.06 g, 13.31 mmol), ethynyltriisopropylsilane (4.5 mL, 20.06 mmol), Cu(I)I (130 mg, 0.683 mmol) and Et$_3$N (8 mL, 57.4 mmol) in DMF (45 mL) was added Pd(PPh$_3$)$_4$ (770 mg, 0.666 mmol). The reaction was heated at 85° C. for 3 h, before being cooled to rt and partitioned between EtOAc (250 mL) and brine (250 mL). The aqueous phase was further extracted with EtOAc (250 mL), then the combined organic extracts were washed with water (3×200 mL) and brine (200 mL), before being dried (MgSO$_4$), filtered and concentrated in vacuo to afford a dark brown oil. The crude product was purified by chromatography on silica gel (220 g column, 0-3% MeOH in DCM) to afford the sub-title compound (5.4 g) as an orange oil.

$^1$H NMR (400 MHz, DMSO-d6) δ: 8.39 (t, 1H), 7.06-7.03 (m, 2H), 6.79-6.78 (m, 1H), 5.43 (s, 2H), 3.54-3.49 (m, 8H), 3.41-3.33 (m, 4H), 3.21 (s, 3H), 1.10 (s, 21H).

LCMS m/z 463 (M+H)$^+$ (ES$^+$)

(iv) 3-Amino-5-ethynyl N (2 (2 (2 methoxyethoxy)ethoxy)ethyl)benzamide

To a stirred solution of the product from step (iii) above (5.33 g, 11.40 mmol) in EtOAc (75 mL) was added 1M TBAF in THF (11.40 mL, 11.40 mmol). The reaction was stirred at rt for 1 h, before being partitioned between water (300 mL) and EtOAc (400 mL), the aqueous phase being further extracted with EtOAc (300 mL). The combined organic extracts were washed with brine (400 mL), before being dried (MgSO$_4$), filtered and concentrated to afford an orange oil. The crude product was dissolved in the minimum quantity of MeOH and loaded onto SCX. The column was eluted with MeOH (3 column volumes) followed by 1% NH$_3$ in MeOH (3 column volumes). The product containing fraction was concentrated in vacuo to afford the sub-title compound (3.27 g) as a brown oil.

$^1$H NMR (400 MHz, DMSO-d6) δ: 8.38 (t, 1H), 7.06-7.04 (m, 2H), 6.75-6.74 (m, 1H), 5.46 (s, 2H), 4.09 (s, 1H), 3.53-3.48 (m, 8H), 3.41-3.39 (m, 2H), 3.37-3.33 (m, 2H), 3.21 (s, 3H).

LCMS m/z 307 (M+H)$^+$ (ES$^+$)

(v) tert-Butyl(4((2-((3-ethynyl-5-((2-(2-(2-methoxyethoxy)ethoxy)ethyl)carbamoyl)phenyl)-amino)pyrimidin-4-yl)oxy)naphthalen-1-yl)carbamate To a stirred solution of the product from step (iv) above (1 g, 3.13 mmol) and tert-butyl(4-((2-chloropyrimidin-4-yl)oxy)naphthalen-1-yl)carbamate (see, for example, Ito, K. et al., WO 2010/067130, 17 Jun. 2010; 777 mg, 2.090 mmol) in DMF (60 mL) was added pTSA monohydrate (200 mg, 1.051 mmol). The resulting solution was stirred at 60° C. for 72 h. The reaction was cooled to rt, then partitioned between EtOAc (150 mL) and sat. aq. NaHCO$_3$ (100 mL). The aqueous layer was further extracted with EtOAc (2×150 mL), then the combined organic extracts were washed with water (3×200 mL) and brine (200 mL), before being dried (MgSO$_4$), filtered and concentrated to afford an orange oil (1.17 g). The crude product was purified by chromatography on silica gel (80 g column, 0-5% MeOH in EtOAc) to afford the sub-title compound (552 mg) as a light brown foam.

$^1$H NMR (400 MHz, DMSO-d6) δ: 9.73 (s, 1H), 9.29 (s, 1H), 8.46-8.43 (m, 2H), 8.11-8.09 (m, 2H), 7.92-7.88 (br m, 1H), 7.83-7.80 (m, 1H), 7.62-7.53 (m, 3H), 7.56-7.55 (m, 1H), 7.42 (d, 1H), 6.57 (d, 1H), 4.14 (s, 1H), 3.54-3.48 (m, 8H), 3.40-3.35 (m, 4H), 3.20 (s, 3H), 1.52 (s, 9H).

LCMS m/z 642 (M+H)$^+$ (ES$^+$)

(vi) 3-((4-((4-Aminonaphthalen-1-yl)oxy)pyrimidin-2-yl)amino)-5-ethynyl-N-(2-(2-(2-methoxy-ethoxy)ethoxy)ethyl)benzamide To a stirred solution of the product from step (v) above (540 mg, 0.825 mmol) in DCM (8 mL) was added TFA (3.2 mL, 41.5 mmol). The reaction was stirred at it for 1 h. The solution was concentrated in vacuo and the resulting oil dissolved in the minimum of MeOH and loaded onto SCX. The column was eluted with MeOH (3 column volumes), then 1% NH$_3$ in MeOH (3 column volumes). The product-containing portion was concentrated in vacuo to afford the sub-title compound (405 mg) as a light, brown foam.

$^1$H NMR (400 MHz, DMSO-d6) δ: 9.73 (s, 1H), 8.45 (t, 1H), 8.36 (d, 1H), 8.14-8.10 (m, 1H), 8.07-8.05 (br m, 1H), 7.94-7.92 (br m, 1H), 7.65-7.61 (m, 1H), 7.47-7.40 (m, 3H), 7.15 (d, 1H), 6.72 (d, 1H), 6.37 (d, 1H), 5.87 (br s, 2H), 4.17 (s, 1H), 3.54-3.48 (m, 8H), 3.40-3.36 (m, 4H), 3.20 (s, 3H).

LCMS m/z 542 (M+H)$^+$ (ES$^+$)

(vii) Phenyl(5-(tert-butyl)-2-methoxy-3-(methylsulfonamido)phenyl)carbamate

Phenyl chloroformate (0.5 mL, 3.99 mmol) was added to a stirred solution of N-(3-amino-5-(tert-butyl)-2-methoxyphenyl)methanesulfonamide (see, for example, Cirillo, P. F. et al., WO 2002/083628, 24 Oct. 2002; 1 g, 3.67 mmol) and NaHCO$_3$ (620 mg, 7.38 mmol) in THF (10 mL) and DCM (10 mL). The mixture was stirred for 2 h then water (20 mL) was added. The organic layer was separated, dried (MgSO$_4$), filtered and evaporated to furnish a brown foam, which was stirred in cyclohexane (20 mL) to afford the sub-title compound (1.4 g) as a colourless solid.

$^1$H NMR (400 MHz, DMSO-d6) δ 9.49 (s, 1H), 9.14 (s, 1H), 7.56 (s, 1H), 7.50-7.37 (m, 2H), 7.31-7.13 (m, 4H), 3.77 (s, 3H), 3.06 (s, 3H), 1.25 (s, 9H)

LCMS m/z 393 (M+H)$^+$ (ES$^+$); 391 (M−H)$^−$ (ES$^−$)

(viii) 3-((4-((4-(3-(5-(tert-Butyl)-2-methoxy-3-(methylsulfonamido)phenyl)ureido)-naphthalen-1-yl)oxy)pyrimidin-2-yl)amino)-5-ethynyl-N-(2-(2-(2-methoxyethoxy)ethoxy)ethyl)benzamide A stirred mixture of phenyl(5-(tert-butyl)-2-methoxy-3-(methylsulfonamido)phenyl)-carbamate (see step 1(vii) above; 95 mg, 0.239 mmol), the product from step (vi) above (120 mg, 0.217 mmol) and Et$_3$N (6 μL, 0.043 mmol) in i-PrOAc (3 mL) was heated at 70° C. overnight. The reaction was cooled to rt and concentrated in vacuo. The remainder was purified by chromatography on silica gel (40 g column, 0-5% MeOH in EtOAc) to afford an oil, which was triturated with diethyl ether to afford a light beige solid. The crude product was purified by preparative HPLC (Varian, Basic (10 mM Ammonium Bicarbonate), Waters X-Bridge Prep-C18, 5 μm, 19×50 mm column, 35-70% MeCN in Water) to afford the title compound (69 mg) as an off-white solid.

$^1$H NMR (400 MHz, DMSO-d6) δ: 9.74 (s, 1H), 9.32 (s, 1H), 9.13 (s, 1H), 8.89 (s, 1H), 8.46-8.43 (m, 2H), 8.26 (d, 1H), 8.17 (d, 1H), 8.09-8.07 (m, 2H), 7.87-7.83 (m, 2H), 7.69-7.65 (m, 1H), 7.61-7.57 (m, 1H), 7.45-7.43 (m, 2H), 7.02 (d, 1H), 6.55 (d, 1H), 4.11 (s, 1H), 3.80 (s, 3H), 3.53-3.47 (m, 8H), 3.40-3.35 (m, 4H), 3.20 (s, 3H), 3.09 (s, 3H), 1.26 (s, 9H).

LCMS m/z 840 (M+H)$^+$ (ES$^+$); 838 (M−H)$^−$ (ES$^−$)

Example 2

3-((4-((4-(3-(5-(tert-Butyl)-2-methoxy-3-(methylsulfonamido)phenyl)ureido)naphthalen-1-yl)oxy)pyrimidin-2-yl)amino)-5-ethynyl-N-(2-(2-(2-methoxyethoxy)ethoxy)ethyl)benzamide (Compound I)

(i) 3-Bromo N (2 (2 (2 methoxyethoxy)ethoxy)ethyl)-5-nitrobenzamide

To a 10 L flask, equipped with a scrubber under nitrogen, was added 3-bromo-5-nitrobenzoic acid (2686 g, 10.91 mol) and thionyl chloride (5.37 L, 75.8 mol). The reaction was heated to 68° C. [GAS EVOLUTION] and was then stirred at 60° C. overnight, after which LC analysis indicated complete reaction. The reaction was cooled to it and concentrated in vacuo to furnish 3.2 kg of material, an amount that indicated the presence of thionyl chloride (100% yield=2.88 kg). The mixture was concentrated from toluene (2×3 L) to remove all traces of thionyl chloride. A total of 3370 g of acid chloride was obtained, with toluene accounting for the excess yield.

To a 20 L flask under nitrogen was added 2-(2-(2-methoxyethoxy)ethoxy)ethanamine (890 g, 5.45 mol) and DCM (3.5 L). This was followed by the addition of 8% aq NaHCO$_3$ (9 L). The acid chloride (1373 g active, 4.89 mol) was then added to the mixture while maintaining the temperature below 25° C. [EXOTHERM and GAS EVOLUTION]. The mixture was stirred for 30 mins, after which LC indicated complete reaction. The organics were separated and washed with 1 M HCl (4.5 L) and 8% aq NaHCO$_3$ (4.5 L), before being dried, filtered and concentrated in vacuo to give a total of 1956 g of the sub-title compound (95% yield). Analysis by $^1$H NMR indicated a product purity of >95%.

(ii) 3-Amino-5-bromo-N-(2-(2-(2-methoxyethoxy)ethoxy)ethyl)benzamide

The product from step (i) above (1 kg, 2.56 mol) was dissolved in THF (3.5 L) and AcOH (500 mL) and hydrogenated at 3 MPa (30 bar) H$_2$ at up to 60° C. with 5% Pt/C (30 g of JM type 18 MA, 55% water). Analysis after 5 hrs showed a 1:1 ratio of ArNHOH and ArNH$_2$. The reaction reached completion after being left overnight, with $^1$H NMR analysis showing 3% des-bromo side product. The catalyst was filtered off, then the residue was diluted with ethyl acetate (3 L) and washed with 20% potassium carbonate solution (3.5 L). The organics were then dried, filtered and concentrated in vacuo to provide a residue that was then slurried in 5 volumes of diethyl ether overnight to reduce the level of the des-bromo species (<2% after the slurry). The sub-title compound was obtained in 90% yield with a purity of 86% by LC.

(iii) 3-Amino-N-(2-(2-(2-methoxyethoxy)ethoxy)ethyl)-5-((triisopropylsilyl)ethynyl)benzamide To a 10 L flask under nitrogen was added the product from step (ii) above (700 g, 1.93 mol) and THF (5.59 L). This was followed by the addition of CuI (19.2 g, 0.1 mol), triethylamine (1.29 L, 9.27 mol) and ethynyltriisopropylsilane (389 g, 2.13 mol). The reaction was degassed and purged with nitrogen three times. Pd(PPh$_3$)$_4$ (125.5 g, 0.198 mol) was added and the reaction degassed and purged with nitrogen. The reaction was heated to 65° C. overnight, after which LC indicated 91% product and <1% starting material. The reaction mixture was concentrated in vacuo, then the residue was taken up in ethyl acetate (2 L) and put through a silica plug (2 kg), eluting with additional ethyl acetate (30 L). The product-containing fractions were concentrated in vacuo, then the crude product was dissolved in TBME (5 L) and extracted with 6 N HCl (5 L). The aqueous HCl phase was washed with TBME (2×5 L), before being basified with 6 N NaOH to pH 9-10. The product was then extracted with TBME (2×5 L), the organics were dried, filtered and concentrated in vacuo to give 635 g of the sub-title compound with a purity of >95% by $^1$H NMR (excluding solvents).

(iv) 3-Amino-5-ethynyl N (2 (2 (2 methoxyethoxy)ethoxy)ethyl)benzamide

To the product from step (iii) above (1200 g, 2.59 mol) in MeCN (8.8 L) was added CsF (433.6 g, 2.85 mol). The reaction was stirred at RT overnight, after which HPLC analysis showed 1.7% product, 97.4% starting material. Additional CsF (420 g, 2.76 mol) was charged and the reaction stirred at RT overnight, whereupon HPLC analysis revealed 91.0% product, 4.4% starting material. The mixture was filtered and the filtrate concentrated in vacuo to give material which was 92.5% product, 0.7% starting material by HPLC. The residue was dissolved in DCM (3 L) and EtOAc (3 L), before being split into two equal portions. Each portion was passed through a silica pad (1.6 kg), eluting with EtOAc (50 L). The filtrates were combined and concentrated in vacuo. The crude material was washed with heptane (2×4 L) to remove silyl impurities. A total of 719 g of sub-title compound was isolated (83% assay by $^1$H NMR, 75% active yield, 597 g active).

(v) tert-Butyl(4-((2-((3-ethynyl-5-((2-(2-(2-methoxy-ethoxy)ethoxy)ethyl)carbamoyl)phenyl)-amino)pyrimidin-4-yl)oxy)naphthalen-1-yl)carbamate Under N$_2$ was charged the product from step (iv) above (301.2 g, 250.0 g active, 0.816 mol), tert-butyl(4-((2-chloropyrimidin-4-yl)oxy)naphthalen-1-yl)carbamate (see, for example, Ito, K. et al., WO 2010/067130, 17 Jun. 2010; 252.8 g, 0.680 mol), pTSA.H$_2$O (24.7 g, 0.130 mol) and THF (7600 mL). The dark red solution was heated to reflux for 6 h then cooled to room temperature, after which HPLC analysis indicated 0.25% the product of step (iv), 22.24% the product of step (vi), 8.98% chloropyrimidine starting material and 64.08% the product of step (v). Further product from step (iv) above (27.1 g, 22.5 g active, 73.4 mmol) was charged and the reaction was heated back to reflux and stirred overnight, with HPLC analysis subsequently revealing 0.20% the product of step (iv), 30.23% the product of step (vi), 4.50% starting chloropyrimidine and 58.61% the product of step (v).

The reaction was cooled to room temperature and quenched with 20% K$_2$CO$_3$ (735 mL), then the layers were separated, with the organic layer being washed with sat. brine (880 mL). The organic layer was dried over MgSO$_4$, filtered and concentrated to isolate a brown sticky solid. Yield=491.2 g (93.8%). HPLC revealed 30.59% the product of step (vi) and 59.50% the product of step (v), with $^1$H NMR conforming to structure.

(vi) 3-((4-((4-Aminonaphthalen-1-yl)oxy)pyrimidin-2-yl)amino)-5-ethynyl-N-(2-(2-(2-methoxy-ethoxy)ethoxy)ethyl)benzamide Under N$_2$ was charged the crude product mixture from step (v) above (491.2 g) and DCM (3700 mL). TFA (695 mL, 12.3 equivalents) was added dropwise, while maintaining the temperature below 20° C. The dark brown solution was stirred at room temperature overnight, following which HPLC analysis indicated 86.90% product of step (vi) and 0.94% product of step (v). The mixture was concentrated and the residue taken up in EtOAc (3700 mL), before being washed with sat. aq. NaHCO$_3$ (2×2000 mL) until a pH of 7-8 was achieved. The organic layer was dried over MgSO$_4$, filtered and concentrated to isolate a purple solid. Yield=360.8 g. HPLC purity 78.58%.

(vii) 5-tert-Butyl-2-methoxy-3-nitroaniline

Under N$_2$ was charged 4-tert-butyl-2,6-dinitroanisole (620 g, 2.439 mol), IMS (4774 mL) and 10% Pd/C (31.8 g). The reaction mixture was heated to reflux (78° C.) and 4-methyl-1-cyclohexene (500 mL, 4.159 mol) was added dropwise over 4.5 h. The reaction was stirred at reflux overnight, whereupon HPLC analysis indicated 72.13% product and 27.17% starting material. Further 4-methyl-1-cyclohexene (160 mL, 1.331 mol) was added dropwise over 3 h and the reaction was stirred at reflux for 72 h. HPLC analysis indicated 92.72% product and 0% starting material. The reaction was cooled to room temperature and the catalyst was removed via vacuum filtration and washed with IMS (500 mL). The solvents were concentrated to ca. 1200 mL to give a ratio of 1:4.45 product:ethanol (target 1:5). 2 M HCl (124 mL) was charged dropwise to the remainder while maintaining the temperature below 23° C. Water (3100 mL) was charged and the resulting suspension was stirred at room temperature for 1.5 h. The solid was collected via vacuum filtration and washed with water (2×1000 mL). The resulting orange needles were dried, under vacuum, at 40° C. overnight. Yield=475.2 g (86.9%). Purity >97% by $^1$H NMR. HPLC purity 98.8%. KF 0.36%.

(viii) N-(5-tert-Butyl-2-methoxy-3-nitrophenyl)methanesulfonamide

Under N$_2$ was charged the product of step (vii) (471 g, 2.099 mol), toluene (1880 mL) and pyridine (471 mL), then methanesulfonyl chloride (179 mL) was added dropwise over 1 h while maintaining the temperature below 35° C. The reaction was stirred at 30-35° C. overnight, before being cooled to below 20° C., then water (1880 mL) and 2 M HCl (1880 mL) were charged (pH 3 achieved). The layers were separated and the organic phase was washed with 2.5% brine (1880 mL). Heptane (3760 mL) was then charged to the organic layer over 0.5 h to isolate a precipitate. The mixture was cooled to 0° C. and stirred for 1 h. The solid was collected via vacuum filtration and washed with heptane (1880 mL), before being dried, under vacuum, at 40° C. overnight. Yield=551 g (87%). HPLC purity 98.5%. Purity >97% by $^1$H NMR.

(ix) N-(3-Amino-5-tert-butyl-2-methoxyphenyl)methanesulfonamide

To a 5 L hydrogenator was charged the product from step (viii) above (209.4 g, 0.693 mol), methanol (1675 mL, 8 volumes) and 10% Pd/C (10.2 g). The vessel was purged with 3×N$_2$ and 3×H$_2$ and then stirred under 0.3447 MPa (50 psi) H$_2$ until no further exotherm was observed, with HPLC indicating 96.35% product and 1.10% starting material. The reaction was diluted with THF (314 mL) and the catalyst was removed via vacuum filtration (Cuno filter), before being washed with THF (1000 mL). The solvents were concentrated to isolate a light brown solid, which was dried under vacuum at 40° C. overnight. Yield=167.0 g (88.5%). HPLC purity 96.7%. Purity >95% by $^1$H NMR.

(x) Phenyl N-[5-tert-butyl-3-(methanesulfonamido)-2-methoxyphenyl]carbamate

Under N$_2$ was charged the product of step (ix) above (167.0 g, 613 mmol), NaHCO$_3$ (77.3 g, 920 mmol), THF (870 mL) and DCM (1440 mL). Phenyl chloroformate (82.6 mL, 659 mmol) was added dropwise, while maintaining the temperature below 20° C., and the reaction was stirred at room temperature for 4 h. HPLC analysis of the reaction mixture indicated 98.6% product and 0.03% starting material. The reaction mixture was filtered and the cake was washed with THF (~50 mL). The filtrate was concentrated to ~900 mL and cyclohexane (2400 mL) was added, then the mixture was left to stir overnight. The resulting solid was collected via vacuum filtration and washed with cyclohexane (500 mL). The pale pink solid produced was dried, under vacuum, at 40° C. for 4 h. Yield=232.6 g (96.7%). HPLC purity 94.5%. $^1$H NMR purity >95%.

(xi) 3-((4-((4-(3-(5-(tert-Butyl)-2-methoxy-3-(methylsulfonamido)phenyl)ureido)naphthalen-1-yl)oxy)pyrimidin-2-yl)amino)-5-ethynyl N (2 (2 (2 methoxyethoxy)ethoxy)ethyl)benzamide Under N$_2$ was charged the product of step (vi) above (175.5 g, 0.324 mol), the product of step (x) above (145.0 g, 0.369 mmol) and iPrOAc (8800 mL). The resulting solution was heated to 60° C. and NEt₃ (9.3 mL) was charged in one portion, then the mixture was left to stir at 60° C. overnight, following which HPLC analysis indicated 25.77% product of step (vi), 3.60% product of step (x) and 57.85% product of step (xi). Further product of step (x) (36.0 g, 0.092 mol) was charged, then the reaction was left to stir at 60° C. overnight, whereupon HPLC analysis indicated 5.47% product of step (vi), 3.72% product of step (x) and 73.33% product of step (xi). The reaction mixture was cooled to room temperature, before being concentrated to isolate a dark purple solid (522.9 g). This solid was recrystallised from acetonitrile (2615 mL, 5 volumes), before being collected via vacuum filtration and washed with iPrOAc (2×500 mL). The pink solid obtained was dried, under vacuum, at 40° C. overnight, yielding 181.1 g (66.5%) of the title compound with HPLC purity 99.27%. ¹H NMR conformed to structure.

Biological Testing: Experimental Methods

Enzyme Binding Assays (Kinomescan)

Kinase enzyme binding activities of compounds disclosed herein may be determined using a proprietary assay which measures active site-directed competition binding to an immobilized ligand (Fabian, M. A. et al., *Nature Biotechnol.*, 2005, 23:329-336). These assays may be conducted by DiscoverX (formerly Ambit; San Diego, Calif.). The percentage inhibition produced by incubation with a test compound may be calculated relative to the non-inhibited control.

Enzyme Inhibition Assays

The enzyme inhibitory activities of compounds disclosed herein are determined by FRET using synthetic peptides labelled with both donor and acceptor fluorophores (Z-LYTE, Invitrogen Ltd., Paisley, UK).

p38 MAPKα Enzyme Inhibition

The following two assay variants can be used for determination of p38 MAPKα inhibition.

Method 1

The inhibitory activities of test compounds against the p38 MAPKα isoform (MAPK14: Invitrogen) are evaluated indirectly by determining the level of activation/phosphorylation of the down-stream molecule, MAPKAP-K2. The p38 MAPKα protein (80 ng/mL, 2.5 μL) is mixed with the test compound (2.5 μL of either 4 μg/mL, 0.4 μg/mL, 0.04 lag/mL or 0.004 μg/mL) for 2 hr at RT. The mix solution (2.5 μL) of the p38α inactive target MAPKAP-K2 (Invitrogen, 600 ng/mL) and FRET peptide (8 μM; a phosphorylation target for MAPKAP-K2) is then added, then the kinase reaction is initiated by adding ATP (40 μM, 2.5 μL). The mixture is incubated for 1 hr at RT. Development reagent (protease, 5 μL) is added for 1 hr prior to detection in a fluorescence microplate reader (Varioskan® Flash, ThermoFisher Scientific).

Method 2

This method follows the same steps as Method 1 above, but utilises a higher concentration of the p38 MAPKα protein (2.5 μL of 200 ng/mL protein instead of 2.5 μL of 80 ng/mL protein) for mixing with the test compound (tested at either 1 μg/mL, 0.1 μg/mL, 0.01 μg/mL or 0.001 μg/mL).

p38 MAPKγ Enzyme Inhibition

The inhibitory activities of compounds of the invention against p38MAPKγ (MAPK12: Invitrogen) are evaluated in a similar fashion to that described hereinabove. The enzyme (800 ng/mL, 2.5 μL) is incubated with the test compound (2.5 μL of either 4 μg/mL, 0.4 μg/mL, 0.04 μg/mL, or 0.004 μg/mL) for 2 hr at RT. The FRET peptide (8 μM, 2.5 μL) and appropriate ATP solution (2.5 μL, 400 μM) are then added to the enzymes/compound mixtures and the whole is incubated for 1 hr. Development reagent (protease, 5 μL) is added for 1 hr prior to detection in a fluorescence microplate reader (Varioskan® Flash, Thermo Scientific).

c-Src and Syk Enzyme Inhibition

The inhibitory activities of the compound of the invention against c-Src and Syk enzymes (Invitrogen) are evaluated in a similar fashion to that described hereinabove. The relevant enzyme (3000 ng/mL or 2000 ng/mL respectively, 2.5 μL) is incubated with the test compound (either 1 μg/mL, 0.1 μg/mL, 0.01 μg/mL, or 0.001 μg/mL, 2.5 μL each) for 2 hr at RT. The FRET peptides (8 μM, 2.5 μL) and appropriate ATP solutions (2.5 μL, 800 μM for c-Src, and 60 μM ATP for Syk) are then added to the enzymes/compound mixtures and the mixture incubated for 1 hr. Development reagent (protease, 5 μL) is added for 1 hr prior to detection in a fluorescence microplate reader (Varioskan® Flash, ThermoFisher Scientific).

GSK 3α Enzyme Inhibition

The following two assay variants can be used for determination of GSK 3α inhibition.

Method 1

The inhibitory activities of the compound of the invention against the GSK 3α enzyme isoform (Invitrogen), are evaluated by determining the level of activation/phosphorylation of the target peptide. The GSK3-α protein (500 ng/mL, 2.5 μL) is mixed with the test compound (2.5 μL at either 4 μg/mL, 0.4 μg/mL, 0.04 μg/mL, or 0.004 μg/mL) for 2 hr at RT. The FRET peptide (8 μM, 2.5 μL), which is a phosphorylation target for GSK3α, and ATP (40 μM, 2.5 μL) are then added to the enzyme/compound mixture and the resulting mixture incubated for 1 hr. Development reagent (protease, 5 μL) is added for 1 hr prior to detection in a fluorescence microplate reader (Varioskan® Flash, ThermoFisher Scientific).

In all cases, the site-specific protease cleaves non-phosphorylated peptide only and eliminates the FRET signal. Phosphorylation levels of each reaction are calculated using the ratio of coumarin emission (donor) over fluorescein emission (acceptor), for which high ratios indicate high phosphorylation and low ratios indicate low phosphorylation levels. The percentage inhibition of each reaction is calculated relative to non-inhibited control and the 50% inhibitory concentration ($IC_{50}$ value) is then calculated from the concentration-response curve.

Method 2

This method follows the same steps as Method 1 above, but utilises a shorter period of mixing of the test compound (105 minutes instead of 2 hours) with the GSK3-α protein. In addition, the concentrations of test compound employed are either 10 μg/mL, 1 μg/mL, 0.1 μg/mL, or 0.01 μg/mL Cellular Assays The compound of the invention was studied using one or more of the following assays.

(a) Inhibition of p38 MAPKα and Lck in Jurkat Cells

Jurkat T cells were cultured in starve medium (RPMI 1640+5% FBS) for 24 h prior to the experiment. Cells were harvested and resuspended at 10×10⁶ cells/mL in starve medium and then plated into round-bottomed 96 well plates at 1×10⁶ cells/well. Serial dilutions of test compound were added (1% final DMSO concentration) for 2 h prior to stimulation. Following pre-incubation with compound, cells were stimulated with $H_2O_2$ (0.05% final) for 5 min. The reaction was stopped by centrifugation at 2000 rpm (3 min, 4° C.), then the supernatant was removed and 100 μL of cold fix/perm solution (BD Fix/Perm kit #554714) added. Plates were incubated for 20 min at 4° C. before centrifugation and washing with supplied 1× wash medium (BD Fix/Perm kit #554714). Cells were stained for either phospho-p38α (T180/182), supplied by Cell Signalling Technology (9211s), or phospho-Lck (Y394), supplied by R&D (MAB7500). Antibodies were diluted to 5 µg/mL (R&D) or 1:200 (Cell Signalling Technology) in wash medium, before being incubated 1 h at 4° C. in the dark. Following 3 repeat washes with ice cold wash buffer, secondary antibody (anti-rabbit-FITC #F1362 or anti-mouse-FITC #F2883, both from Sigma) was added at a dilution of 1:1000 and incubated for 1 h at 4° C. in the dark. Cells were washed 3× times in cold wash buffer then, following a final wash in cold PBS, were resuspended in 150 µL cold PBS. Cells were analysed by flow cytometry using BD Accuri C6.

(aa) LPS-induced TNFα/IL-8 Release in d-U937 Cells

U937 cells, a human monocytic cell line, are differentiated to macrophage-type cells by incubation with phorbol myristate acetate (PMA; 100 ng/mL) for 48 to 72 hr. Cells are pre-incubated with final concentrations of test compound for 2 hr and are then stimulated with 0.1 tag/mL of LPS (from *E. Coli*: 0111:B4, Sigma) for 4 hr. The supernatant is collected for determination of TNFα and IL-8 concentrations by sandwich ELISA (Duo-set, R&D systems). The inhibition of TNFα production is calculated as a percentage of that achieved by 10 µg/mL of BIRB796 at each concentration of test compound by comparison against vehicle control. The relative 50% effective concentration ($REC_{50}$) is determined from the resultant concentration-response curve. The inhibition of IL-8 production is calculated at each concentration of test compound by comparison with vehicle control. The 50% inhibitory concentration ($IC_{50}$) is determined from the resultant concentration-response curve.

(b) LPS-induced TNFα/IL-8 Release in PBMC Cells

Peripheral blood mononuclear cells (PBMCs) from healthy subjects are separated from whole blood using a density gradient (Lymphoprep, Axis-Shield Healthcare). The PBMCs are seeded in 96 well plates and treated with the compound of the invention at the desired concentration for 2 hours before addition of 1 ng/mL LPS (*Escherichia Coli* 0111:B4 from Sigma Aldrich) for 24 hours under normal tissue culture conditions (37° C., 5% $CO_2$). The supernatant is harvested for determination of IL-8 and TNFα concentrations by sandwich ELISA (Duo-set, R&D systems) and read on the fluorescence microplate reader (Varioskan® Flash, ThermoFisher Scientific). The concentration at 50% inhibition ($IC_{50}$) of IL-8 and TNFα production is calculated from the dose response curve.

(c) IL-2 and IFN Gamma Release in CD3/CD28 Stimulated PBMC Cells

PBMCs from healthy subjects are separated from whole blood using a density gradient (Lymphoprep, Axis-Shield Healthcare). Cells are added to a 96 well plate pre-coated with a mixture of CD3/CD28 monoclonal antibodies (0.3 µg/mL eBioscience and 3 µg/mL BD Pharmingen respectively). Compound at the desired concentration is then added to the wells and the plate left for 3 days under normal tissue culture conditions. Supernatants are harvested and IL-2 and IFN gamma release determined by Sandwich ELISA (Duo-set, R&D System). The $IC_{50}$ is determined from the dose response curve.

(d) IL-1β-Induced IL-8 Release in HT29 Cells

HT29 cells, a human colon adenocarcinoma cell line, are plated in a 96 well plate (24 hr) and pre-treated with the compound of the invention at the desired concentration for 2 hours before addition of 5 ng/mL of IL-1β (Abcam) for 24 hours. Supernatants are harvested for IL-8 quantification by Sandwich ELISA (Duo-set, R&D System). The $IC_{50}$ is determined from the dose response curve.

(e) LPS-Induced IL-8 and TNFα Release in Primary Macrophages

PBMCs from healthy subjects are separated from whole blood using a density gradient (Lymphoprep, Axis-Shield Healthcare). Cells are incubated for 2 hrs and non-adherent cells removed by washing. To differentiate the cells to macrophages, they are incubated with 5 ng/mL of GM-CSF (Peprotech) for 7 days under normal tissue culture conditions. The compound of the invention is then added to the cells at the desired concentration for a 2 hour pre-treatment before stimulation with 10 ng/mL LPS for 24 hours. Supernatants are harvested and IL-8 and TNFα release determined by Sandwich ELISA (Duo-set, R&D System). The $IC_{50}$ is determined from the dose response curve.

(f) Poly I:C-Induced ICAM-1 Expression in BEAS2B Cells

Poly I:C is used in these studies as a simple, RNA virus mimic. Poly I:C-Oligofectamine mixture (1 µg/mL Poly I:C, ±2% Oligofectamine, 25 µL; Invivogen Ltd., San Diego, Calif., and Invitrogen, Carlsbad, Calif., respectively) is transfected into BEAS2B cells (human bronchial epithelial cells, ATCC). Cells are pre-incubated with final concentrations of the test compound for 2 hr and the level of ICAM1 expression on the cell surface is determined by cell-based ELISA. At a time point 18 hr after poly I:C transfection, cells are fixed with 4% formaldehyde in PBS and then endogenous peroxidase is quenched by the addition of washing buffer (100 µL, 0.05% Tween in PBS: PBS-Tween) containing 0.1% sodium azide and 1% hydrogen peroxide. Cells are washed with washbuffer (3×200 µL) and after blocking the wells with 5% milk in PBS-Tween (100 µL) for 1 hr, the cells are incubated with anti-human ICAM-1 antibody (50 µL; Cell Signalling Technology, Danvers, Mass.) in 1% BSA PBS overnight at 4° C.

The cells are washed with PBS-Tween (3×200 µL) and incubated with the secondary antibody (100 µL; HRP-conjugated anti-rabbit IgG, Dako Ltd., Glostrup, Denmark). The cells are then incubated with substrate (50 µL) for 2-20 min, followed by the addition of stop solution (50 µL, 1N $H_2SO_4$). The ICAM-1 signal is detected by reading the absorbance at 450 nm against a reference wavelength of 655 nm using a spectrophotometer. The cells are then washed with PBS-Tween (3×200 µL) and total cell numbers in each well are determined by reading absorbance at 595 nm after Crystal Violet staining (50 µL of a 2% solution in PBS) and elution by 1% SDS solution (100 µL) in distilled water. The measured OD 450-655 readings are corrected for cell number by dividing with the OD595 reading in each well. The inhibition of ICAM-1 expression is calculated at each concentration of test compound by comparison with vehicle control. The 50% inhibitory concentration ($IC_{50}$) is determined from the resultant concentration-response curve.

(g) Cell Mitosis Assay

Peripheral blood mononucleocytes (PBMCs) from healthy subjects are separated from whole blood (Quintiles, London, UK) using a density gradient (Histopaque®-1077, Sigma-Aldrich, Poole, UK). The PBMCs (3 million cells per sample) are subsequently treated with 2% PHA (phytohaemagglutinin, Sigma-Aldrich, Poole, UK) for 48 hr, followed by a 20 hr exposure to varying concentrations of the test compound. At 2 hr before collection, PBMCs are treated with demecolcine (0.1 µg/mL; Invitrogen, Paisley, UK) to arrest cells in metaphase. To observe mitotic cells, PBMCs are permeabilised and fixed by adding Intraprep (50 µL; Beckman Coulter, France), and stained with anti-phospho-histone 3 (0.26 ng/L; #9701; Cell Signalling, Danvers, Mass.) and propidium iodide (1 mg/mL; Sigma-Aldrich, Poole, UK) as previously described (Muehlbauer P. A. and Schuler M. J., Mutation Research, 2003, 537:117-130). Fluorescence is observed using an ATTUNE flow cytometer (Invitrogen, Paisley, UK), gating for lymphocytes. The percentage inhibition of mitosis is calculated for each treatment relative to vehicle (0.5% DMSO) treatment.

(h) Rhinovirus-Induced IL-8 Release and ICAM-1 Expression

Human rhinovirus RV16 is obtained from the American Type Culture Collection (Manassas, Va.). Viral stocks are generated by infecting HeLa cells with HRV until 80% of the cells are cytopathic.

BEAS2B cells are infected with HRV at an MOI of 5 and incubated for 2 hr at 33° C. with gentle shaking to promote absorption. The cells are then washed with PBS, fresh media added and the cells are incubated for a further 72 hr. The supernatant is collected for assay of IL-8 concentrations using a Duoset ELISA development kit (R&D systems, Minneapolis, Minn.).

The level of ICAM-1 expressing cell surface is determined by cell-based ELISA. At 72 hr after infection, cells are fixed with 4% formaldehyde in PBS. After quenching endogenous peroxidase by adding 0.1% sodium azide and 1% hydrogen peroxide, wells are washed with wash-buffer (0.05% Tween in PBS: PBS-Tween). After blocking well with 5% milk in PBS-Tween for 1 hr, the cells are incubated with anti-human ICAM-1 antibody in 5% BSA PBS-Tween (1:500) overnight. Wells are washed with PBS-Tween and incubated with the secondary antibody (HRP-conjugated anti-rabbit IgG, Dako Ltd.). The ICAM-1 signal is detected by adding substrate and reading at 450 nm with a reference wavelength of 655 nm using a spectrophotometer. The wells are then washed with PBS-Tween and total cell numbers in each well are determined by reading absorbance at 595 nm after Crystal Violet staining and elution with 1% SDS solution. The measured $OD_{450-655}$ readings are corrected for cell number by dividing with the $OD_{595}$ reading in each well. Compounds are added 2 hr before HRV infection and 2 hr after infection when noninfected HRV is washed out.

(i) Assessment of HRV16 induced Cytopathic Effect (CPE) in MRC5 Cells

MRC5 cells are infected with HRV16 at an MOI of 1 in DMEM containing 5% FCS and 1.5 mM $MgCl_2$, followed by incubation for 1 hr at 33° C. to promote adsorption. The supernatants are aspirated, and then fresh media added followed by incubation for 4 days. Where appropriate, cells are pre-incubated with compound or DMSO for 2 hr, and the compounds and DMSO added again after washout of the virus.

Supernatants are aspirated and incubated with methylene blue solution (100 μL, 2% formaldehyde, 10% methanol and 0.175% Methylene Blue) for 2 hr at RT. After washing, 1% SDS in distilled water (100 μL) is added to each well, and the plates are shaken lightly for 1-2 hr prior to reading the absorbance at 660 nm. The percentage inhibition for each well is calculated. The $IC_{50}$ value is calculated from the concentration-response curve generated by the serial dilutions of the test compounds.

(j) In Vitro RSV Virus Load in Primary Bronchial Epithelial Cells

Normal human bronchial epithelial cells (NHBEC) grown in 96 well plates are infected with RSV A2 (Strain A2, HPA, Salisbury, UK) at a MOI of 0.001 in the LHC8 Media:RPMI-1640 (50:50) containing 15 mM magnesium chloride and incubated at 37° C. for adsorption. The cells are then washed with PBS (3×200 μL), then fresh media (200 μL) is added and incubation continued for 4 days. Where appropriate, cells are pre-incubated with the compound or DMSO for 2 hr, and then added again after washout of the virus.

The cells are fixed with 4% formaldehyde in PBS solution (50 μL) for 20 min, washed with WB (3×200 μL) (washing buffer, PBS including 0.5% BSA and 0.05% Tween-20) and incubated with blocking solution (5% condensed milk in PBS) for 1 hr. Cells are then washed with WB (3×200 μL) and incubated for 1 hr at RT with anti-RSV (2F7) F-fusion protein antibody (40 μL; mouse monoclonal, lot 798760, Cat. No. ab43812, Abcam) in 5% BSA in PBS-tween. After washing, cells are incubated with an HRP-conjugated secondary antibody solution (50 μL) in 5% BSA in PBS-Tween (lot 00053170, Cat. No. P0447, Dako) and then TMB substrate added (50 μL; substrate reagent pack, lot 269472, Cat. No. DY999, R&D Systems, Inc.). This reaction is stopped by the addition of 2N $H_2SO_4$ (50 μL) and the resultant signal is determined colourimetrically (OD: 450 nm with a reference wavelength of 655 nm) in a microplate reader (Varioskan® Flash, ThermoFisher Scientific).

Cells are then washed and a 2.5% crystal violet solution (50 μL; lot 8656, Cat. No. PL7000, Pro-Lab Diagnostics) is applied for 30 min. After washing with WB, 1% SDS in distilled water (100 μL) is added to each well, and plates are shaken lightly on the shaker for 1 hr prior to reading the absorbance at 595 nm. The measured $OD_{450-655}$ readings are corrected to the cell number by dividing the $OD_{450-655}$ by the $OD_{595}$ readings. The percentage inhibition for each well is calculated and the $IC_{50}$ value is calculated from the concentration-response curve generated from the serial dilutions of compound.

(k) Cell Viability Assay: MTT Assay

Differentiated U937 cells are pre-incubated with each test compound (final concentration 1 μg/mL or 10 μg/mL in 200 μL media indicated below) under two protocols: the first for 4 hr in 5% FCS RPMI1640 media and the second in 10% FCS RPMI1640 media for 24 h. The supernatant is replaced with new media (200 μL) and MTT stock solution (10 μL, 5 mg/mL) is added to each well. After incubation for 1 hr the media are removed, DMSO (200 μL) is added to each well and the plates are shaken lightly for 1 hr prior to reading the absorbance at 550 nm. The percentage loss of cell viability is calculated for each well relative to vehicle (0.5% DMSO) treatment. Consequently an apparent increase in cell viability for drug treatment relative to vehicle is tabulated as a negative percentage.

(l) Human Biopsy Assay

Intestinal mucosa biopsies are obtained from the inflamed regions of the colons of IBD patients. The biopsy material is cut into small pieces (2-3 mm) and placed on steel grids in an organ culture chamber at 37° C. in a 5% $CO_2$/95% $O_2$ atmosphere in serum-free media. DMSO control or test compound at the desired concentration are added to the tissue and incubated for 24 hr in the organ culture chamber. The supernatant is harvested for determination of IL-6, IL-8, IL-1β and TNFα levels by R&D ELISA. Percentage inhibition of cytokine release by the test compound is calculated relative to the cytokine release determined for the DMSO control (100%).

s (m) Accumulation of β Catenin in d-U937 Cells

U937 cells, a human monocytic cell line, are differentiated into macrophage-type cells by incubation with PMA (100 ng/mL) for between 48 to 72 hr. The cells are then incubated with either final concentrations of test compound or vehicle for 18 hr. The induction of β-catenin by the test compound is stopped by replacing the media with 4% formaldehyde solution. Endogenous peroxide activity is neutralised by incubating with quenching buffer (100 μL, 0.1% sodium azide, 1% $H_2O_2$ in PBS with 0.05% Tween-20) for 20 min. The cells are washed with washing buffer (200 μL; PBS containing 0.05% Tween-20) and incubated with blocking solution (200 μL; 5% milk in PBS) for 1 hr, re-washed with washing buffer (200 μL) and then incubated overnight with anti-β-catenin antibody solution (50 μL) in 1% BSA/PBS (BD, Oxford, UK).

After washing with washing buffer (3×200 μL; PBS containing 0.05% Tween-20), cells are incubated with a HRP-conjugated secondary antibody solution (100 μL) in 1% BSA/PBS (Dako, Cambridge, UK) and the resultant signal is determined colourimetrically (OD: 450 nm with a reference wavelength of 655 nm) using TMB substrate (50 μL; R&D Systems, Abingdon, UK). This reaction is stopped by addition of 1N $H_2SO_4$ solution (50 μL). Cells are then washed with washing buffer and 2% crystal violet solution (50 μL) is applied for 30 min. After washing with washing buffer (3×200 μL), 1% SDS (100 μL) is added to each well and the plates are shaken lightly for 1 hr prior to measuring the absorbance at 595 nm (Varioskan® Flash, Thermo-Fisher Scientific).

The measured $OD_{450-655}$ readings are corrected for cell number by dividing the $OD_{450-655}$ by the $OD_{595}$ readings. The percentage induction for each well is calculated relative to vehicle, and the ratio of induction normalised in comparison with the induction produced by a standard control comprising the Reference compound N-(4-(4-(3-(3-tert-butyl-1-p-tolyl-1H-pyrazol-5-yl)ureido)naphthalen-1-yloxy)pyridin-2-yl)-2-methoxyacetamide (1 μg/mL), which is defined as unity.

(n) T Cell Proliferation

PBMCs from healthy subjects are separated from whole blood using a density gradient (Lymphoprep, Axis-Shield Healthcare). The lymphocyte fraction is first enriched for CD4+ T cells by negative magnetic cell sorting as per the manufacturer's instructions (Miltenyi Biotec 130-091-155). Naïve CD4+ T cells are then separated using positive magnetic selection of CD45RA+ cells using microbeads as per the manufacturer's instructions (130-045-901). Cells are plated at $2\times10^5$ cells per well in 100 μL RPMI/10% FBS on 96 well flat bottomed plate (Corning Costar). 25 μL of test compound are diluted to the appropriate concentration (8× final concentration) in normal medium and added to duplicate wells on the plate to achieve a dose response range of 0.03 ng/mL-250 ng/mL. DMSO is added as a negative control. Plates are allowed to pre-incubate for 2 hours before stimulation with 1 μg/mL anti-CD3 (OKT3; eBioscience). After 72 h, the medium in each well is replaced with 150 μL of fresh medium containing 10 μM BrdU (Roche). After 16 h, the supernatant is removed, the plate is dried and the cells fixed by adding 100 μL of fix/denature solution to each well for 20 min as per the manufacturer's instructions (Roche). Plates are washed once with PBS before addition of the anti-BrdU detection antibody and incubated for 90 mins at room temperature. Plates are then washed gently 3× with the wash buffer supplied and developed by addition of 100 μL of substrate solution. The reaction is stopped by addition of 50 μL of 1 M $H_2SO_4$ and read for absorbance at 450 nm on a plate reader (Varioskan® Flash, ThermoFisher Scientific). The $IC_{50}$ is determined from the dose response curve.

(o) IL-2 and IFNγ Release in CD3/CD28 Stimulated LPMC Cells from IBD Patients

*Lamina propria* mononuclear cells (LPMCs) are isolated and purified from inflamed IBD mucosa of surgical specimens or from normal mucosa of surgical specimens as follows: The mucosa is removed from the deeper layers of the surgical specimens with a scalpel and cut in fragments of size 3-4 mm. The epithelium is removed by washing the tissue fragments three times with 1 mM EDTA (Sigma-Aldrich, Poole, UK) in HBSS (Sigma-Aldrich) with agitation using a magnetic stirrer, discarding the supernatant after each wash. The sample is subsequently treated with type 1A collagenase (1 mg/mL; Sigma-Aldrich) for 1 h with stirring at 37° C. The resulting cell suspension is then filtered using a 100 μm cell strainer, washed twice, resuspended in RPMI-1640 medium (Sigma-Aldrich) containing 10% fetal calf serum, 100 U/mL penicillin and 100 μg/mL streptomycin, and used for cell culture.

Freshly isolated LPMCs ($2\times10^5$ cells/well) are stimulated with 1 μg/mL α-CD3/α-CD28 for 48 h in the presence of either DMSO control or appropriate concentrations of compound. After 48 h, the supernatant is removed and assayed for the presence of TNFα and IFNγ by R&D ELISA. Percentage inhibition of cytokine release by the test compound is calculated relative to the cytokine release determined for the DMSO control (100%).

(p) Inhibition of Cytokine Release from Myofibroblasts Isolated from IBD Patients Myofibroblasts from inflamed IBD mucosa are isolated as follows:

The mucosa is dissected and discarded and 1 mm-sized mucosal samples are cultured at 37° C. in a humidified $CO_2$ incubator in Dulbecco's modified Eagle's medium (DMEM, Sigma-Aldrich) supplemented with 20% FBS, 1% non-essential amino acids (Invitrogen, Paisley, UK), 100 U/mL penicillin, 100 μg/mL streptomycin, 50 tag/mL gentamycin, and 1 μg/mL amphotericin (Sigma-Aldrich). Established colonies of myofibroblasts are seeded into 25-$cm^2$ culture flasks and cultured in DMEM supplemented with 20% FBS and antibiotics to at least passage 4 to provide a sufficient quantity for use in stimulation experiments.

Subconfluent monolayers of myofibroblasts, seeded in 12-well plates at $3\times10^5$ cells per well, are starved in serum-free medium for 24 h at 37° C., 5% $CO_2$, before being cultured for 24 h in the presence of either DMSO control or appropriate concentrations of compound. After 24 h, the supernatant is removed and assayed for the presence of IL-8 and IL-6 by R&D ELISA. Percentage inhibition of cytokine release by the test compound is calculated relative to the cytokine release determined for the DMSO control (100%).

(q) Human Neutrophil Degranulation

Neutrophils are isolated from human peripheral blood as follows:

Blood is collected by venepuncture and anti-coagulated by addition of 1:1 EDTA:sterile phosphate buffered saline (PBS, no Ca+/Mg+). Dextran (3% w/v) is added (1 part dextran solution to 4 parts blood) and the blood allowed to stand for approximately 20 minutes at rt. The supernatant is carefully layered on a density gradient (Lymphoprep, Axis-Shield Healthcare) and centrifuged (15 mins, 2000 rpm, no brake). The supernatant is aspirated off and the cell pellet is re-suspended in sterile saline (0.2%) for no longer than 60 seconds (to lyse contaminating red blood cells). 10 times volume of PBS is then added and the cells centrifuged (5 mins, 1200 rpm). Cells are re-suspended in HBSS+(Hanks buffered salt solution (without phenol red) containing cytochalasin B (5 μg/mL) and 1 mM $CaCl_2$) to achieve $5\times10^6$ cells/mL.

$5 \times 10^4$ cells are added to each well of a V-bottom 96 well plate and are incubated (30 mins, 37° C.) with the appropriate concentration of test compound (0.3-1000 ng/mL) or vehicle (DMSO, 0.5% final conc). Degranulation is stimulated by addition of fMLP (final conc 1 μM). After a further incubation (30 mins, 37° C.), the cells are removed by centrifugation (5 mins, 1500 rpm) and the supernatants transferred to a flat bottom 96 well plate. An equal volume of tetramethylbenzidine (TMB) is added and, after 10 mins, the reaction terminated by addition of an equal volume of sulphuric acid (0.5 M) and absorbance read at 450 nm (background at 655 nm subtracted). The 50% inhibitory concentration ($IC_{50}$) is determined from the resultant concentration-response curve.

(r) Cell Cytotoxicity Assay $5 \times 10^4$ TK6 cells (lymphoblastic T cell line) are added to the appropriate number of wells of a 96 well plate in 195 μL of media (RPMI supplemented with 10% foetal bovine serum). 5 μL of DMSO control (final concentration 0.5% v/v) or test compound (final concentration either 5 or 1 μg/mL) is added to the wells and incubated at 37° C., 5% $CO_2$. After 24 hours, the plate is centrifuged at 1300 rpm for 3 minutes and the supernatant discarded. Cells are then resuspended in 7.5 μg/mL propidium iodide (PI) in PBS. After 15 minutes, cells are analysed by flow cytometry (BD accuri). The % viability is calculated as the % of cells that are PI negative in the test wells normalised to the DMSO control.

In Vivo Screening: Pharmacodynamics and Anti-Inflammatory Activity (i) LPS-Induced Neutrophil Accumulation in Mice Non-fasted Balb/c mice are dosed by the intra tracheal route with either vehicle, or the test substance at the indicated times (within the range 2-8 hr) before stimulation of the inflammatory response by application of an LPS challenge. At T=0, mice are placed into an exposure chamber and exposed to LPS (7.0 mL, 0.5 mg/mL solution in PBS) for 30 min. After a further 8 hr, the animals are anesthetized, their tracheas cannulated and BALF extracted by infusing and then withdrawing from their lungs 1.0 mL of PBS via the tracheal catheter. Total and differential white cell counts in the BALF samples are measured using a Neubaur haemocytometer. Cytospin smears of the BALF samples are prepared by centrifugation at 200 rpm for 5 min at RT and stained using a DiffQuik stain system (Dade Behring). Cells are counted using oil immersion microscopy. Data for neutrophil numbers in BAL are represented as mean±S.E.M. (standard error of the mean). The percentage inhibition of neutrophil accumulation is calculated for each treatment relative to vehicle treatment.

(ii) Cigarette Smoke Model

A/J mice (males, 5 weeks old) are exposed to cigarette smoke (4% cigarette smoke, diluted with air) for 30 min/day for 11 days using a Tobacco Smoke Inhalation Experiment System for small animals (Model SIS-CS; Sibata Scientific Technology, Tokyo, Japan). Test substances are administered intra-nasally (35 μL of solution in 50% DMSO/PBS) once daily for 3 days after the final cigarette smoke exposure. At 12 hr after the last dosing, each of the animals is anesthetized, the trachea cannulated and bronchoalveolar lavage fluid (BALF) is collected. The numbers of alveolar macrophages and neutrophils are determined by FACS analysis (EPICS® ALTRA II, Beckman Coulter, Inc., Fullerton, Calif., USA) using anti-mouse MOMA2 antibody (macrophage) or anti-mouse 7/4 antibody (neutrophil).

(iii) DSS-Induced Colitis in Mice

Non-fasted, 10-12 week old, male BDF1 mice are dosed by oral gavage twice daily with either vehicle, reference item (5-ASA) or test compound one day before (Day −1) stimulation of the inflammatory response by treatment with dextran sodium sulphate (DSS). On Day 0 of the study, DSS (5% w/v) is administered in the drinking water followed by BID dosing of the vehicle (5 mL/kg), reference (100 mg/kg) or test compound (5 mg/kg) for 7 days. The drinking water with DSS is replenished every 3 days. During the study, animals are weighed every day and stool observations are made and recorded as a score, based on stool consistency. At the time of sacrifice on Day +6, the large intestine is removed and the length and weight are recorded. Sections of the colon are taken for either MPO analysis, to determine neutrophil infiltration, or for histopathology scoring, to determine disease severity.

(iv) TNBS-Induced Colitis in Mice

Non-fasted, 10-12 week old, male BDF1 mice are dosed by oral gavage twice daily with either vehicle (5 mL/kg), reference item (Budesonide 2.5 mg/kg) or test compound (1 or 5 mg/kg) one day before (Day −1) stimulation of the inflammatory response by treatment with 2,4,6-trinitrobenzenesulphonic acid (TNBS) (15 mg/mL in 50% ethanol/50% saline). On Day 0 of the study, TNBS (200 μL) is administered intracolonically via a plastic catheter with BID dosing of the vehicle, reference or test compound continuing for 2 or 4 days. During the study, animals are weighed every day and stool observations are made and recorded as a score, based on stool consistency. At the time of sacrifice on Day 2 (or Day 4), the large intestine is removed and the length and weight recorded. Sections of the colon are taken for histopathology scoring to determine disease severity.

(v) Adoptive Transfer in Mice

On Study day 0, female Balb/C mice are terminated and spleens obtained for $CD45RB^{high}$ cell isolation (Using SCID IBD cell Separation protocol). Approximately $4 \times 10^5$ cells/mL $CD45RB^{high}$ cells are then injected intraperitoneally (100 μL/mouse) into female SCID animals. On study day 14, mice are weighed and randomized into treatment groups based on body weight. On Day 14, the compound is administered BID, via oral gavage, in a vehicle comprising a defined mixture of corn oil (32.5%), transcutol (20%), maisine (12.5%) and cremophor ELP (35%) at the dose levels outlined below in Tables 6a and 6b and a dose volume of 5 mL/kg. Treatment continues until study day 42, at which point the animals are necropsied 4 hours after the morning administration. The colon length and weight are recorded and used as a secondary endpoint in the study as a measurement of colon oedema. The colon is then divided into six cross-sections, four of which are used for histopathology scoring (primary endpoint) and two are homogenised for cytokine analysis. Data shown is the % inhibition of the induction window between naïve animals and vehicle animals, where higher inhibition implies closer to the non-diseased, naïve, phenotype.

(vi) Endotoxin-Induced Uveitis in Rats

Male Lewis rats (6-8 weeks old, Charles River UK Limited) are housed in cages of 3 at 19-21° C. with a 12 h light/dark cycle (07:00/19:00) and fed a standard diet of rodent chow and water ad libitum. Non-fasted rats are weighed, individually identified on the tail with a permanent marker, and receive a single intravitreal administration into the right vitreous humor (5 µL dose volume) of 100 ng/animal of LPS (*Escherichia coli* 0111:B4 prepared in PBS, Sigma Aldrich, UK) using a 32-gauge needle. Untreated rats are injected with PBS. Test compound, dexamethasone (Dex) or vehicle (20% hydroxypropyl-β-cyclodextrin, 0.1% HPMC, 0.01% Benzalkonium chloride, 0.05% EDTA, 0.7% NaCl in deionised water) are administered by the topical route onto the right eye (10 µL) of animals 30 minutes prior to LPS, at the time of LPS administration, and 1, 2 and 4 hours post LPS administration. Before administration, the solution or suspension to be administered is agitated for 5 minutes to ensure a uniform suspension. 6 hours after LPS dosing, animals are euthanized by overdose with pentobarbitone (i.v.). Following euthanasia, the right eye of each animal is enucleated and dissected into front (anterior) and back (posterior) sections around the lens. Each section is weighed and homogenised in 500 µL of sterile phosphate buffered saline followed by 20 minutes centrifugation at 12000 rpm at 4° C. The resulting supernatant is divided into 3 aliquots and stored at −80° C. until subsequent cytokine analysis by R&D DuoSet ELISA.

Summary of In Vitro and In Vivo Screening Results

TABLE 1a

Dissociation constants for selected kinases determined by LeadHunter Discover Services (DiscoveRx Corporation, Fremont, CA) using the KINOMEscan ™ technology.

| Test Article | Dissociation Constant (nM) | | |
|---|---|---|---|
| | Lck | p38 MAPKα | Syk |
| Compound I | 4.1 | 9 | 21 |

Studies conducted by LeadHunter Discover Services (DiscoveRx Corporation, Fremont, Calif.) using the KINOMEscan™ technology determined that the compound of the examples (Compound I) did not have any significant effect on the binding of the kinases B-Raf and B-Raf (V600E) to their standard ligands. Moreover, that compound showed substantially improved selectivity compared to the Reference Compound N-(4-(4-(3-(3-tert-butyl-1-p-tolyl-1H-pyrazol-5-yl) ureido)-naphthalen-1-yloxy)pyridin-2-yl)-2-methoxyacetamide (WO 2010/112936), as evidenced by lower selectivity scores (Table 1b).

TABLE 1b

KinomeScan Selectivity score data at 50 and 500 nM; KinomeScan Selectivity Scores/number of individual kinase hits

| Compound | 50 nM | | | 500 nM | | |
|---|---|---|---|---|---|---|
| | S(35) | S(10) | S(1) | S(35) | S(10) | S(1) |
| Reference Compound | 0.174/67 | 0.083/32 | 0.018/7 | 0.370/143 | 0.272/105 | 0.117/45 |
| Compound I | 0.068/27 | 0.023/9 | 0.000/0 | 0.197/78 | 0.129/51 | 0.038/15 |

S(35) = (number of non-mutant kinases with % Ctrl <35)/(number of non-mutant kinases tested);
S(10) = (number of non-mutant kinases with % Ctrl <10)/(number of non-mutant kinases tested);
S(1) = (number of non-mutant kinases with % Ctrl <1)/(number of non-mutant kinases tested)

TABLE 1c

Results from in vitro p38 MAPKα (Method 2), c-Src, Syk and GSK3α (Method 2) inhibition assays

| Test Compound | $IC_{50}$ Values for Enzyme Inhibition (nM) | | | |
|---|---|---|---|---|
| | p38 MAPKα | c-Src | Syk | GSK3α |
| Compound I | 224 | 24 | 591 | 411 |

TABLE 1d

Data from phosphoflow assays evaluating cellular p38 MAPKα and Lck inhibition

| Test Article | $IC_{50}$ Values (ng/mL) | |
|---|---|---|
| | phospho-p38 MAPKα | phospho-Lck |
| Compound I | 20 | 6 |

TABLE 2

Inhibition of cytokine release in stimulated cells (assays (b), (c) and (d) above).

| | $IC_{50}$ Values for Inhibition of Cytokine Release (nM) | | | | | | |
|---|---|---|---|---|---|---|---|
| | dU937 cells | | PBMCs | | | | HT29 cells |
| Test Article | IL-8 | TNFα | IL-8 | TNFα | IL-2 | IFNγ | IL-8 |
| Compound I | — | — | 1.5 | — | 74.0 | 7.3 | 8.0 |

As illustrated in Table 3 below, Compound I was also screened in cellular assay (I), i.e., the ex-vivo human biopsy model described above, where it demonstrated significant anti-inflammatory effects in biopsies from ulcerative colitis (UC) patients. In contrast to healthy volunteers, intestinal mucosal biopsies from UC patients have been shown to spontaneously release pro-inflammatory cytokines in vitro (Onken, J. E. et al., *J Clin Immunol*, 2008, 126(3): 345-352). Thus, Compound I significantly inhibited cytokine (IL-1β, IL-6 and IL-8) release compared to the DMSO control when incubated, at 1 µg/mL, for 24 hours with biopsies from ulcerative colitis patients.

TABLE 3

Summary of results from assays using intestinal mucosa biopsies from the inflamed regions of the colon of various patients suffering from ulcerative colitis (a form of IBD).

| | | Cytokine release from biopsies of UC patients | | | | |
|---|---|---|---|---|---|---|
| Treatment group | n | IL-1β release | n | IL-6 release | n | IL-8 release |
| DMSO control | | 100% | | 100% | | 100% |
| Compound I (1 µg/mL) | 4 | 5 ± 8 | 4 | 17 ± 23 | 2 | 9 ± 15 |

As illustrated in Table 4a below, Compound I is markedly less active than the Reference Compound (N-(4-(4-(3-(3-tert-butyl-1-p-tolyl-1H-pyrazol-5-yl)ureido)naphthalen-1-yloxy)pyridin-2-yl)-2-methoxyacetamide, WO 2010/112936) in assay (g) above, which measures impact on cell division (mitosis) in PBMCs.

TABLE 4a

Effect of Compound I on cell division in PBMCs in comparison to the Reference compound

| Test compound | % Inhibition of mitosis at 5 µg/mL |
|---|---|
| Reference compound | 87.8[a] |
| Compound I | 20.5 |

[a]See, for example, the value reported in WO 2013/050757.

As illustrated in Table 4b below, Compound I did not elicit any substantial β-catenin induction when studied in assay (m) above. Thus, the potential of the compound to increase cellular concentrations of β-catenin was found to be negative in that its inductive effect at various test concentrations was substantially less than the effect produced by the Reference Compound at 1 µg/mL.

TABLE 4b

Effect of Compound I on β-catenin induction in comparison to the Reference compound (NT = not tested)

| | % β-catenin induction Concentration of test compound | | |
|---|---|---|---|
| Test compound | 1 µg/mL | 5 µg/mL | 10 µg/mL |
| Reference compound | 100 | NT | NT |
| Compound I | 21 | 14 | 26 |

As illustrated in Table 5 below, Compound I was also screened in in vivo assay (iv) above, as conducted over 2 days and employing a self-microemulsifying drug delivery system (SMEDDS) as vehicle comprising a defined mixture of corn oil (32.5%), transcutol (20%), maisine (12.5%) and cremophor ELP (35%). Histopathology analysis revealed that Compound I displayed activity in this in vivo model of colonic inflammation. In particular, when dosed orally at 5 mg/kg, Compound I demonstrated marked improvements in ulcer grade and epithelial repair compared to the vehicle control. Furthermore, it produced a marked reduction in inflammatory cell infiltrate in the reticular and laminar propria zones.

TABLE 5

Effect of Compound I on TNBS-induced colitis in mice.

| | | TNBS | |
|---|---|---|---|
| Treatment group | n | Ulcer grade | LP inflammation |
| Non-diseased | 6 | 0.0 ± 0.0 | 0.2 ± 0.2 |
| TNBS + Vehicle | 24 | 4.4 ± 0.4 | 4.8 ± 0.4 |
| TNBS + Compound I | 12 | 3.6 ± 0.5 | 3.8 ± 0.4 |

As illustrated in Tables 6a and 6b below, Compound I was also screened in the in vivo (adoptive transfer) assay (v) above. Analysis of the relative ratios of colon weight to length in naïve, control and treated animals at the end of the study revealed that Compound I displayed significant activity in this T cell driven in vivo model of colonic inflammation.

TABLE 6a

Summary of results from adoptive transfer mouse model.

| Treatment group | Dose | Colon weight:length | % Inhibition |
|---|---|---|---|
| Naïve | N/A | 0.022 ± 0.001 | 100 |
| Cyclosporin A | 75 mg/kg | 0.029 ± 0.001 | 64 |
| Vehicle control | N/A | 0.042 ± 0.005 | 0 |
| Compound I | 3 mg/kg | 0.024 ± 0.003 | 90 |

TABLE 6b

Summary of further results from an additional study in the adoptive transfer mouse model.

| Treatment group | n | Colon weight:length |
|---|---|---|
| Non-diseased | 4 | 0.021 ± 0.001 |
| Vehicle control | 12 | 0.047 ± 0.004 |
| Compound I (3 mg/kg) | 12 | 0.034 ± 0.003 |
| Compound I (0.3 mg/kg) | 12 | 0.041 ± 0.005 |
| Compound I (0.03 mg/kg) | 12 | 0.033 ± 0.002 |

As illustrated in Table 6c below, Compound I also significantly reduced levels of pro-inflammatory cytokines in samples of colon tissue from mice in the adoptive transfer model.

TABLE 6c

Summary of cytokine level measurements from adoptive transfer mouse model.

| Treatment group | n | IFNγ(pg/mL) | IL-8 (pg/mL) |
|---|---|---|---|
| Non-diseased | 4 | 1.3 ± 0.6 | 7.9 ± 0.9 |
| Vehicle control | 12 | 117.7 ± 36.6 | 1064.9 ± 239.6 |
| Compound I (3 mg/kg) | 12 | 10.8 ± 3.3 | 70.8 ± 22.8 |

Summary of Additional Studies

Determination of Pharmacokinetic Parameters

Studies were conducted by Sai Life Sciences (Hinjewadi, Pune, India) to investigate the plasma pharmacokinetics and total colon tissue distribution of Compound I. In particular, pharmacokinetic studies were carried out in:

- male C57BL/6 mice, following a single oral administration; and
- male Wistar rats following a single intravenous or oral administration.

The data reveal that Compound I achieves substantial colonic concentrations, while plasma exposures are very low or negligible.

TABLE 8a

Median plasma concentrations (ng/mL) obtained following oral administration of Compound I to mice at 5 mg/kg.

| Test article | Vehicle | Time (h) | | | | | | |
|---|---|---|---|---|---|---|---|---|
| | | 1 | 2 | 4 | 6 | 8 | 12 | 24 |
| Compound I | B | 0.0 | 0.0 | 0.0 | 0.0 | 0.0 | 0.0 | 0.0 |

Key
Vehicle B=Corn oil-Transcutol-Maisine-Cremophor ELP (32.5:20:12.5:35), a self-microemulsifying drug delivery system (SMEDDS).

TABLE 8b

Median total colon concentrations (ng/g) obtained following oral administration of Compound I to mice at 5 mg/kg (vehicle B is as in respect of Table 8a).

| Test article | Vehicle | Time (h) | | | | | | |
|---|---|---|---|---|---|---|---|---|
| | | 1 | 2 | 4 | 6 | 8 | 12 | 24 |
| Compound I | B | 0.0 | 10.4 | 420 | 3080 | 1951 | 126 | 23 |

TABLE 9a

Pharmacokinetic data obtained following intravenous administration of Compound I to rats at 0.25 mg/kg in 5% DMSO-7.5% Solutol HS15-87.5% normal saline.

| Test article | $C_0$ (ng/mL) | $AUC_{last}$ (h*ng/mL) | $AUC_{INF}$ (h*ng/mL) | $T_{1/2}$ (h) | Cl (mL/min/kg) | $V_{ss}$ (L/kg) |
|---|---|---|---|---|---|---|
| Compound I | 6536 | 869 | 871 | 0.1 | 4.8 | 0.03 |

TABLE 9b

Pharmacokinetic data obtained following oral administration of Compound I to rats at 5 mg/kg.

| Test article | Vehicle | $T_{max}$ (h) | $C_{max}$ (ng/mL) | $AUC_{last}$ (h*ng/mL) | $AUC_{INF}$ (h*ng/mL) | $F_{po}$ (%) |
|---|---|---|---|---|---|---|
| Compound I | B | NC[‡] | NC[‡] | NC[‡] | NC[‡] | 0.0 |

Key
Vehicle B=as in respect of Table 8a.
[‡] Not calculated because no compound was detected in plasma.

TABLE 9c

Median plasma concentrations (ng/mL) obtained following oral administration of Compound I to rats at 5 mg/kg

| Test article | Vehicle | Time (h) | | | | | | | | |
|---|---|---|---|---|---|---|---|---|---|---|
| | | 0.25 | 0.5 | 1 | 2 | 4 | 6 | 8 | 12 | 24 |
| Compound I | B | 0.0 | 0.0 | 0.0 | 0.0 | 0.0 | 0.0 | 0.0 | 0.0 | 0.0 |

Key
Vehicle B is as in respect of Table 8a.

Determination of ADME Parameters

Assessment of certain in vitro ADME (absorption, distribution, metabolism, and excretion) parameters for Compound I was conducted by BioFocus (Saffron Walden, UK). The results reveal that Compound I is cleared rapidly by human hepatocytes and that it has a reduced liability for time-dependent cytochrome P450 inhibition.

TABLE 10

Data from human hepatocyte stability test for Compound I

| Test article | $T_{1/2}$ (min) | Mean intrinsic clearance (μL/min/million cells) | Mean hepatic extraction ratio |
|---|---|---|---|
| Compound I | 34 | 41 | 0.85 |

TABLE 11a

Summary of CYP3A4 inhibition studies for Compound I (results reported are the arithmetic mean of two experiments).

| Test article | 0 min preincubation | | 30 min preincubation | |
|---|---|---|---|---|
| | $IC_{50}$ (μM) | 15 μM % Inh | $IC_{50}$ (μM) | 15 μM % Inh |
| Ref Cpd A | >15 | 41 | 0.4 | 92 |
| Compound I | >15 | 31 | 7.8 | 54 |

Key
Ref Cpd A: 1-(4-((2-((7-methyl-1H-indazol-5-yl)amino)pyrimidin-4-yl)oxy)-naphthalen-1-yl)-3-(3-(2-methyl-but-3-yn-2-yl)-1-(p-tolyl)-1H-pyrazol-5-yl)urea (Fyfe, M. C. T., et al. WO 2014/033447).

TABLE 11b

Summary of CYP2C9 inhibition studies for Compound I (results reported are the arithmetic mean of two experiments).

| | 0 min preincubation | | 30 min preincubation | |
|---|---|---|---|---|
| Test article | IC$_{50}$ (µM) | 15 µM % Inh | IC$_{50}$ (µM) | 15 µM % Inh |
| Ref Cpd A | >5 | 31[†] | 1.4 | 66[†] |
| Compound I | >15 | 21 | >15 | 37 |

Key
Ref Cpd A: as in respect of Table 11a.
[†] Precipitation observed at 15 µM, therefore inhibition at 5 µM reported instead.

hERG Inhibition Studies

Compound I was tested for inhibition of the human ether a go-go (hERG) channel using IonWorks™ patch clamp electrophysiology at Essen Bioscience (Welwyn Garden City, England).

TABLE 12 hERG inhibition data for Compound I

| Test article | IC$_{50}$ (µM) | % Inhibition at 3 µM |
|---|---|---|
| Compound I | >3.0 | −12 ± 4 |

Analysis of Metabolites

Studies were conducted by BioFocus (Saffron Walden, UK) to determine the metabolic fate of Compound I following incubation with rat, Cynomolgus macaque or human hepatocytes.

Separate incubations (n=3) of Compound I (10 µM initial concentration) or DMSO control, were performed with cryopreserved hepatocytes from each species (0.5 million cell/mL) at 37° C. for 0, 60 and 90 minutes before termination of reactions and compound extraction with acetonitrile. Sample replicates were pooled prior to analysis.

Potential metabolites were identified using time-of-flight (TOF) and triple quadruple (TQ) mass spectrometers.

The results reveal that Compound I forms 9 metabolites in hepatocytes, 8 of which result from oxidation on the polyethylene glycol chain of the amide moiety. The other metabolite, seen principally in cynomolgus macaque hepatocytes, arises via oxidation on the 5-(tert-butyl)-2-methoxy-3-(methylsulfonamido)phenyl fragment. Thus, no products were noted that could be connected to metabolism at the naphthalene moiety, a phenomenon that results in the hepatotoxicity associated with p38α inhibitor BIRB796 (Iwano, S., et al., *J. Appl. Toxicol.* 2011, 31, 671-677). All metabolites identified in human hepatocyte incubations were also detected in either rat or cynomolgus macaque hepatocyte incubations.

Mutagenicity Assessment (Bacterial Reverse Mutation Screen)

Studies were conducted by Sequani (Ledbury, Herefordshire, UK) to assess Compound I for its ability to induce mutations in two histidine dependent auxotrophic mutants of *Salmonella typhimurium*, strains TA98 and TA100 in vitro.

The mutation screen was conducted using the plate incorporation method and was performed in both the presence and absence of S-9 mix (a liver post-mitochondrial fraction derived from the livers of Aroclor 1254 treated rats). The bacteria were exposed to the test compound dissolved in dimethylsulphoxide, which solvent was also used as the negative control. The dose levels used were 0.32, 1.6, 8, 40, 200, 1000 or 5000 µg/plate.

Analysable treatment levels of test compound were limited by insolubility to 1000 µg/plate, as heavy precipitation observed at 5000 µg/plate affected the scoring of the colonies.

Precipitation was also noted in both strains at 1000 µg/plate in the presence and absence of S-9 mix.

Compound I produced no dose-related or statistically significant increases in revertant colonies in either *Salmonella typhimurium* strain in the presence or absence of S-9 mix.

Hydrolytic Stability Study

Chemical stability of Compound I was assessed in a mixture of DMSO and water (3:1) at a test compound concentration of 1 mg/mL General HPLC Procedure
Agilent, Waters X-Select C18, 2.5 µm, 4.6×30 mm column, 4 min method, 5-95%
MeCN/water (0.1% formic acid).
Flow rate 2.5 ml/min.
Column Oven Temperature 40° C.
Detection 254 nm.
Sample Preparation
A 1.0 mg sample of test compound was dissolved in 750 µL of DMSO. Water (250 µL) was added slowly, ensuring no precipitation occurred.
Recording Stability
A 50 µL aliquot of the test solution was removed and analysed in duplicate by 5 µL HPLC injections. The peak area for the test compound was recorded following manual integration of the corresponding UV trace.
The test solution was heated to 60° C., with stirring, and 50 µL aliquots removed for HPLC analysis at 5 and 24 h timepoints. In all cases, 5 µL injections were used and the samples analysed in duplicate.
The peak areas for the test compounds were recorded at both subsequent timepoints and the % decomposition calculated from the % change in peak area over time.
Reference Compound B (3-ethynyl-5-((4-((4-(3-(3-isopropyl-1-(p-toly)-1H-pyrazol-5-yl)ureido)naphthalen-1-yl)oxy)pyrimidin-2-yl)amino)-N-(2-morpholinoethyl)benzamide; Cariou, C. A. M., et al, WO 2014/027209) was included in the stability study as a control to validate the study. In contrast to the compound of the present invention, which was completely stable, this Reference Compound underwent substantial decomposition under the conditions of the experiment.
The results of the study are reported in the table below.

| Test Compound | Time (min) | % Parent Remaining |
|---|---|---|
| Reference Compound B | 0 | 100 |
| | 300 | 82 |
| | 1440 | 36 |
| Compound I | 0 | 100 |
| | 300 | 100 |
| | 1440 | 100 |

ABBREVIATIONS

AcOH glacial acetic acid
aq aqueous
5-ASA 5-aminosalicylic acid
ATP adenosine-5'-triphosphate
BALF bronchoalveolar lavage fluid
BID bis in die (twice-daily)
BINAP 2,2'-bis(diphenylphosphino)-1,1'-binaphthyl
BOP (benzotriazol-1-yloxy)tris(dimethylamino)phosphonium hexafluorophosphate br broad
BrdU 5-bromo-2'-deoxyuridine
BSA bovine serum albumin
CatCart® catalytic cartridge
CDI 1,1-carbonyl-diimidazole
COPD chronic obstructive pulmonary disease
d doublet
dba dibenzylideneacetone
DBU 1,8-diazabicyclo[5.4.0]undec-7-ene
DCC dicyclohexylcarbodiimide
DCM dichloromethane
IAD diisopropyl azodicarboxylate
DIPEA diisopropylethylamine
DMAP 4-dimethylaminopyridine
DMEM Dulbecco's modified eagle medium
DMF N,N-dimethylformamide
DMSO dimethyl sulfoxide
DPPA diphenylphosphoryl azide
d-U937 cells PMA differentiated U-937 cells
EDTA ethylenediaminetetraacetic acid
ELISA enzyme-linked immunosorbent assay
(ES$^-$) electrospray ionization, negative mode
(ES$^+$) electrospray ionization, positive mode
Et ethyl
Et$_3$N triethylamine
EtOAc ethyl acetate
EtOH ethanol
FACS fluorescence-activated cell sorting
FBS foetal bovine serum
FCS foetal calf serum
fMLP formyl-methionyl-leucyl-phenylalanine
FRET fluorescence resonance energy transfer
GSK3α glycogen synthase kinase 3α
HBEC primary human bronchial epithelial cells
HBSS Hank's balanced salt solution
HPLC high performance liquid chromatography
HPMC hydroxypropylmethylcellulose
h or hr hour(s)
HATU 2-(1H-7-azabenzotriazol-1-yl)-1,1,3,3-tetramethyluronium hexafluorophosphate
HOAt 1-hydroxy-7-azabenzotriazole
HOBt hydroxybenzotriazole
HRP horseradish peroxidise
HRV human rhinovirus
ICAM-1 inter-cellular adhesion molecule 1
IFNγ interferon-γ
IL interleukin
IMS industrial methylated spirit
iPrOAc isopropyl acetate
JNK c-Jun N-terminal kinase
LC liquid chromatography
Lck lymphocyte-specific protein tyrosine kinase
LPS lipopolysaccharide
m multiplet
(M+H)$^+$ protonated molecular ion
MAPK mitogen-activated protein kinase
MAPKAP-K2 mitogen-activated protein kinase-activated protein kinase-2
mCPBA meta-chloroperbenzoic acid
Me methyl
MeCN acetonitrile
MeOH methanol
MHz megahertz
min or mins minute(s)
MMAD mass median aerodynamic diameter
MOI multiplicity of infection
MPO myeloperoxidase
MTT 3-(4,5-dimethylthiazol-2-yl)-2,5-diphenyltetrazolium bromide
MS mass spectrometry
m/z mass-to-charge ratio
NMP N-methylpyrrolodinone
NMR nuclear magnetic resonance (spectroscopy)
OD optical density
PBMC peripheral blood mononuclear cell
PBS phosphate buffered saline
Ph phenyl
PHA phytohaemagglutinin
PMA phorbol myristate acetate
pTSA 4-methylbenzenesulfonic acid (para-toluenesulfonic acid)
PyBOP (benzotriazol-1-yloxy)tripyrrolidinophosphonium hexafluorophosphate
q quartet
rt or RT room temperature
RP HPLC reverse phase high performance liquid chromatography
rpm revolutions per minute
RPMI Roswell Park Memorial Institute
RSV respiratory syncytical virus
s singlet
sat or satd saturated
SCID severe combined immunodeficiency
SCX solid supported cation exchange (resin)
SDS sodium dodecyl sulfate
S$_N$Ar nucleophilic aromatic substitution
Syk Spleen tyrosine kinase
t triplet
T3P 1-propanephosphonic acid cyclic anhydride
TBAF tetrabutylammonium fluoride
TBDMS tert-butyldimethylsilyl
TBME tert-butyl methyl ether
TCID$_{50}$ 50% tissue culture infectious dose
TEA triethylamine
THF tetrahydrofuran
TFA trifluoroacetic acid
TGFβ transforming growth factor beta
TIPS triisopropylsilyl
TMB 3,3',5,5'-tetramethylbenzidine
TMS-Cl trimethylsilyl chloride
TNFα tumor necrosis factor alpha Prefixes n-, s-, i-, t- and tert- have their usual meanings: normal, secondary, iso, and tertiary.

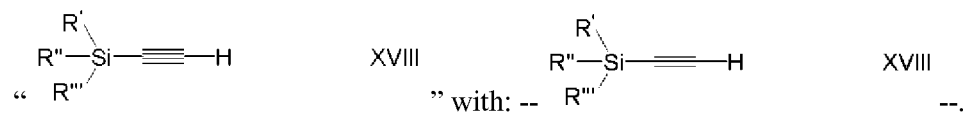

The invention claimed is:
1. A compound of formula I,

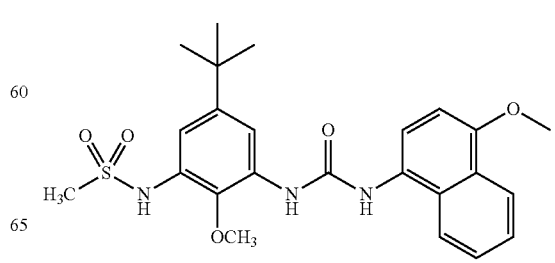

-continued

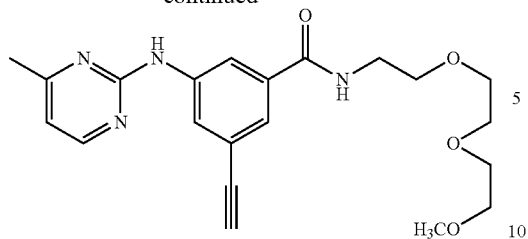

or a pharmaceutically acceptable salt thereof.

2. A compound according to claim 1 that is:
3-((4-((4-(3-(5-(tert-butyl)-2-methoxy-3-(methylsulfonamido)phenyl)ureido)naphthalen-1-yl)oxy)pyrimidin-2-yl)amino)-5-ethynyl-N-(2-(2-(2-methoxyethoxy)ethoxy)ethyl)-benzamide.

3. A pharmaceutical formulation comprising a compound as defined in claim 1, or pharmaceutically acceptable salt thereof, in admixture with a pharmaceutically acceptable adjuvant, diluent or carrier.

4. A combination product comprising
(A) a compound as defined in claim 1, or pharmaceutically acceptable salt thereof, and
(B) another therapeutic agent,
wherein each of components (A) and (B) is formulated in admixture with a pharmaceutically-acceptable adjuvant, diluent or carrier.

5. A process for the preparation of a compound of formula I which process comprises:
(a) reaction of a compound of formula II,

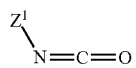

with a compound of formula III,

wherein one of $Z^1$ and $Z^2$ is a structural fragment of formula IV

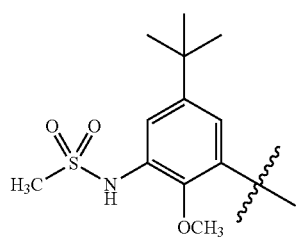

and the other of $Z^1$ and $Z^2$ is a structural fragment of formula V

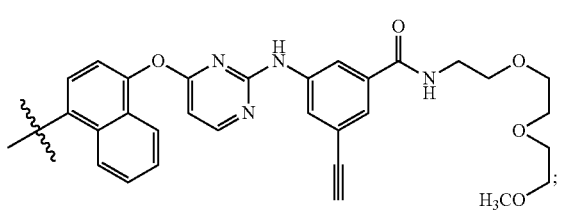

(b) reaction of a compound of formula IIa,

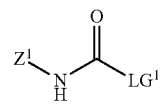

wherein $Z^1$ is as defined above, with a suitable azide-forming agent,
which reaction is followed, without isolation, by thermal rearrangement of the intermediate acyl azide (of formula $Z^1$—C(O)—$N_3$) to provide, in situ, a compound of formula II, which compound is then reacted with a compound of formula III as defined above;
(c) reaction of a compound of formula IIb,

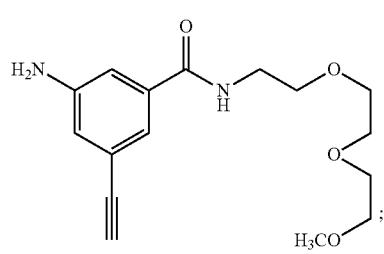

wherein $LG^1$ represents a leaving group and $Z^1$ is as defined above, with a compound of formula III, as defined above;
(d) reaction of a compound of formula VI,

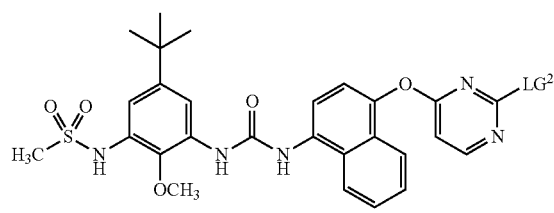

wherein $LG^2$ represents a leaving group, with a compound of formula VII,

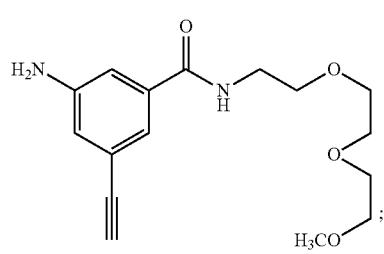

or
(e) reaction of a compound of formula VIIa,
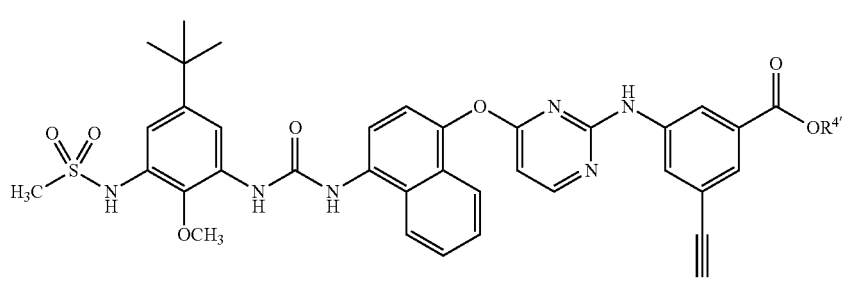
wherein $R^{4'}$ represents H or a $C_{1-3}$ alkyl group, with a compound of formula VIIb, $H_2N-[CH_2CH_2-O]_2-CH_2CH_2-OCH_3$ VIIb.
6. A process as claimed in claim 4, which process comprises reaction of a compound of formula XV
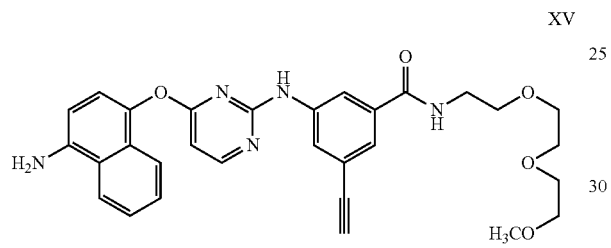
with a compound of formula XVI,
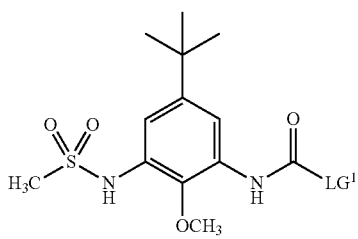
wherein $LG^1$ is as defined in claim 4.
* * * * *

UNITED STATES PATENT AND TRADEMARK OFFICE
CERTIFICATE OF CORRECTION

PATENT NO. : 8,927,563 B2
APPLICATION NO. : 14/242531
DATED : January 6, 2015
INVENTOR(S) : Matthew Colin Thor Fyfe It is certified that error appears in the above-identified patent and that said Letters Patent is hereby corrected as shown below:

In the Specification

In column 1 at line 60, change "MAPKαrβ" to --MAPKα/β--.

In column 8 at lines 51-52, change "pregelatinated" to --pregelatinized--.

In column 8 at line 58, change "poly-vinylpyrollidone;" to --poly-vinylpyrrolidone;--.

In column 12 at line 63, change "bisalazide);" to --balsalazide);--.

In column 16 at line 52 (approx.), change "VIIIa," to --VIIa,--.

In column 17 at line 19, change "VIIIa" to --VIIa--.

In column 17 at line 22, change "VIIIa" to --VIIa--.

In column 27 at lines 40-41 (approx.), change "3-Amino N-(2 (2 (2 methoxyethoxy)ethoxy)ethyl)-5-((triisopropyl)ethynyl)benzamide" to --3-Amino-N-(2-(2-(2-methoxyethoxy)ethoxy)ethyl)-5-((triisopropyl)ethynyl)benzamide--.

In column 27 at lines 62-63 (approx.), change "3-Amino-5-ethynyl N (2 (2 (2 methoxyethoxy)ethoxy)ethyl)benzamide" to --3-Amino-5-ethynyl-N-(2-(2-(2-methoxyethoxy)ethoxy)ethyl)benzamide--.

In column 28 at lines 18-20 (approx.), change "tert-Butyl(4((2-((3-ethynyl-5-((2-(2-(2-methoxyethoxy)ethoxy)ethyl)carbamoyl)phenyl)-amino)pyrimidin-4-yl)oxy)naphthalen-1-yl)carbamate" to --tert-Butyl(4-((2-((3-ethynyl-5-((2-(2-(2-methoxyethoxy)ethoxy)ethyl)carbamoyl)phenyl)-amino)pyrimidin-4-yl)oxy)naphthalen-1-yl)carbamate--.

In column 28 at line 49, change "at it" to --at rt--.

In column 29 at lines 48-49 (approx.), change "3-Bromo N (2 (2 (2 methoxyethoxy)ethoxy)ethyl)-5-nitrobenzamide" to --3-Bromo-N-(2-(2-(2-methoxyethoxy)ethoxy)ethyl)-5-nitrobenzamide--.

Signed and Sealed this
Twelfth Day of January, 2016

Michelle K. Lee
*Director of the United States Patent and Trademark Office*

CERTIFICATE OF CORRECTION (continued)
U.S. Pat. No. 8,927,563 B2

In column 29 at line 56, change "to it" to --to rt--.

In column 30 at lines 51-52 (approx.), change "3-Amino-5-ethynyl N (2 (2 (2 methoxyethoxy)ethoxy)ethyl)benzamide" to --3-Amino-5-ethynyl-N-(2-(2-(2-methoxyethoxy)ethoxy)ethyl)benzamide--.

In column 32 at lines 60-63, change "3-((4-((4-(3-(5-(tert-Butyl)-2-methoxy-3-(methylsulfonamido)phenyl)ureido)naphthalen-1-yl)oxy)pyrimidin-2-yl)amino)-5-ethynyl N (2 (2 (2 methoxyethoxy)ethoxy)ethyl)benzamide" to --3-((4-((4-(3-(5-(tert-Butyl)-2-methoxy-3-(methylsulfonamido)phenyl)ureido)naphthalen-1-yl)oxy)pyrimidin-2-yl)amino)-5-ethynyl-N-(2-(2-(2-methoxyethoxy)ethoxy)ethyl)benzamide--.

In column 33 at line 42, change "lag/mL" to --$\mu$g/mL--.

In column 35 at line 18, change "tag/mL" to --$\mu$g/mL--.

In column 38 at line 56, change "s (m)" to --(m)--.

In column 40 at line 33, change "tag/mL" to --$\mu$g/mL--.

In column 41 at line 46 (approx.), change "Neubaur" to --neubauer--.

In column 52 at line 25 (approx.), change "syncytical" to --syncytial--.

In the Claims

In column 54 at line 12 (approx.), in claim 5, change "Ha," to --IIa,--.

In column 55 at line 21 (approx.), in claim 6, change "claim 4," to --claim 5,--.

In column 56 at line 31 (approx.), in claim 6, change "claim 4." to --claim 5.--.

UNITED STATES PATENT AND TRADEMARK OFFICE
CERTIFICATE OF CORRECTION

| | | |
|---|---|---|
| PATENT NO. | : 8,927,563 B2 | Page 1 of 4 |
| APPLICATION NO. | : 14/242531 | |
| DATED | : January 6, 2015 | |
| INVENTOR(S) | : Matthew Colin Thor Fyfe | |

It is certified that error appears in the above-identified patent and that said Letters Patent is hereby corrected as shown below:

In The Specification

At column 18, line 21 to column 19, line 9, please replace:

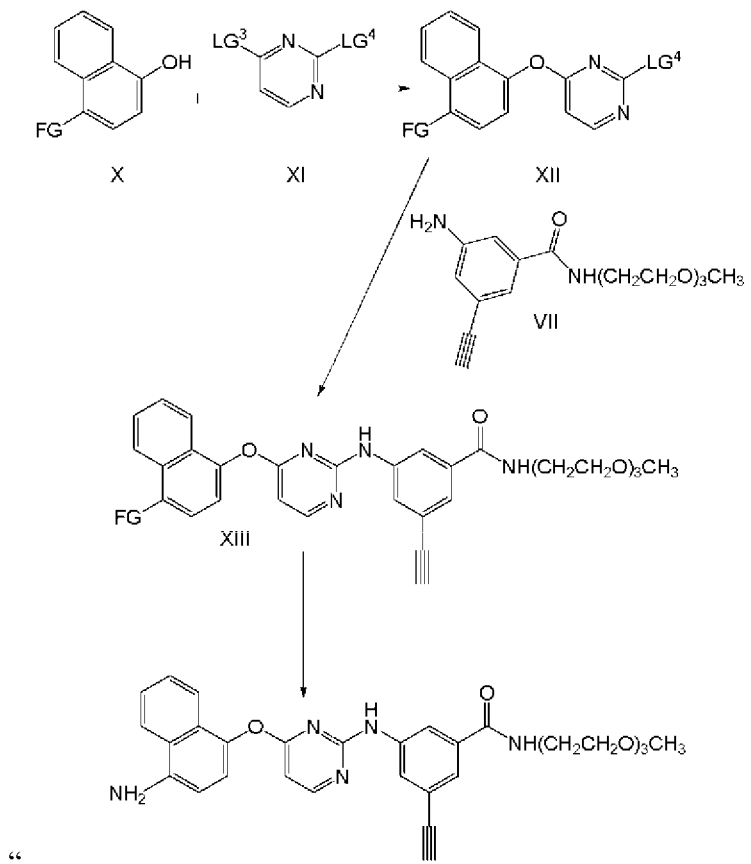

" "

Signed and Sealed this
Twelfth Day of July, 2016

Michelle K. Lee
*Director of the United States Patent and Trademark Office* with:
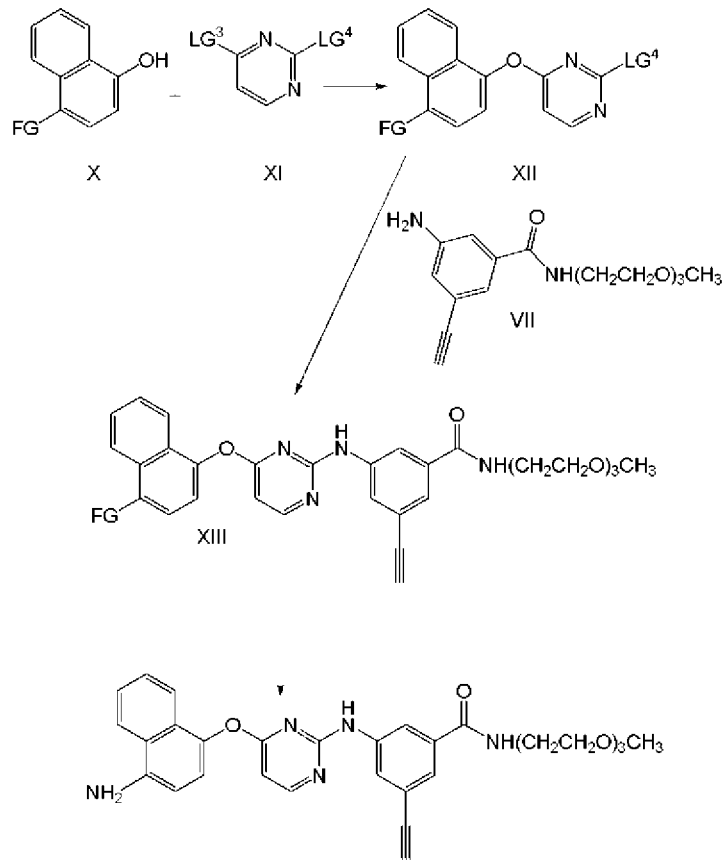
At column 19, line 40, please replace:
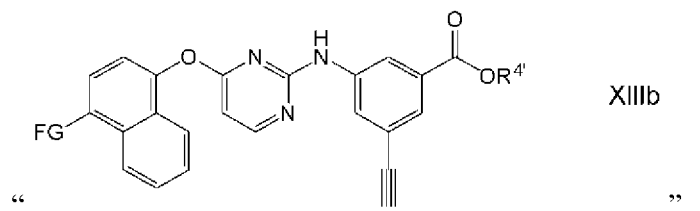
"                                                                          "
with:
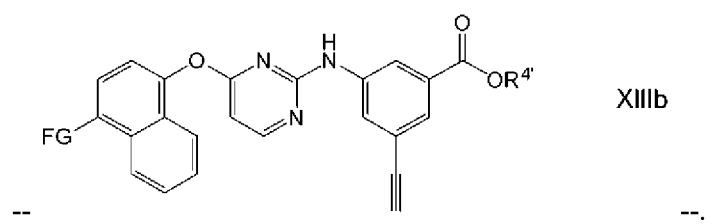
--                                                                          --.

CERTIFICATE OF CORRECTION (continued)
U.S. Pat. No. 8,927,563 B2

At column 20, line 15, please replace:

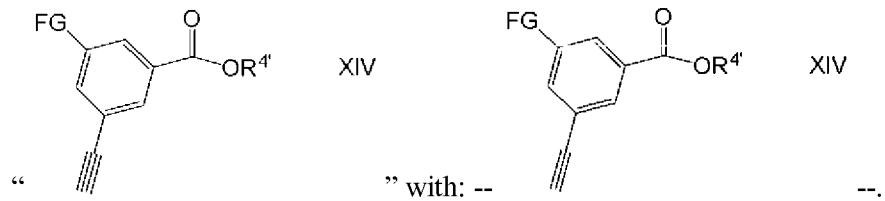

" with: --    --.

At column 20, line 60, please replace:

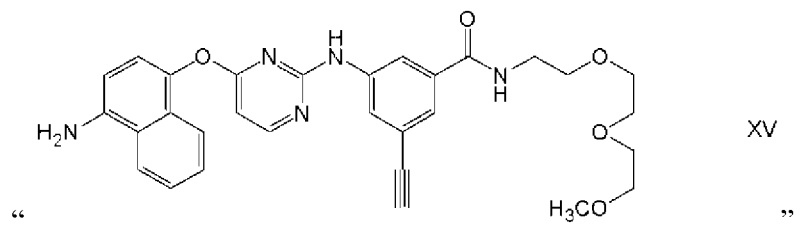

"                              "

with:

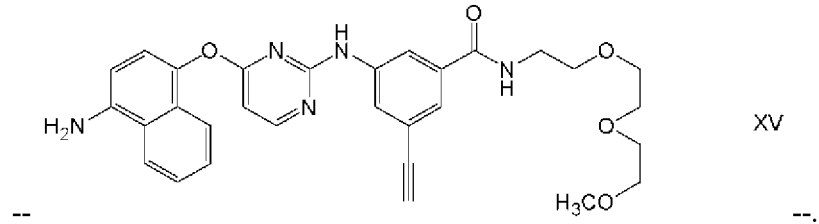

--                             --.

At column 21, line 25, please replace:

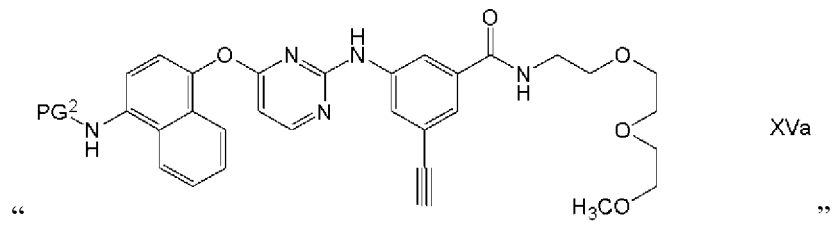

"                              "

with:

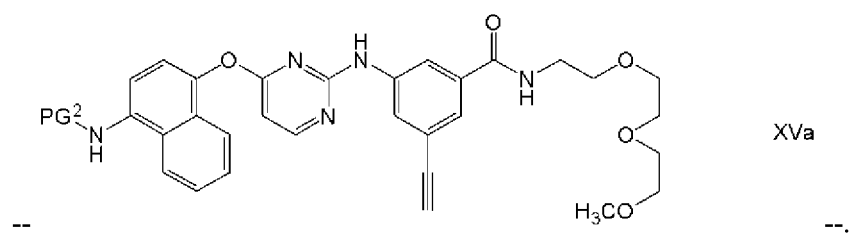

--                             --.

CERTIFICATE OF CORRECTION (continued)
U.S. Pat. No. 8,927,563 B2

At column 21, line 55, please replace:

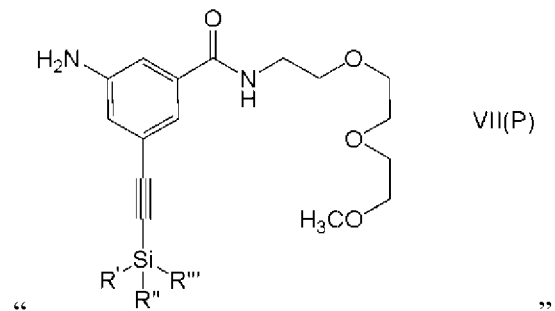
"                                  "

with:

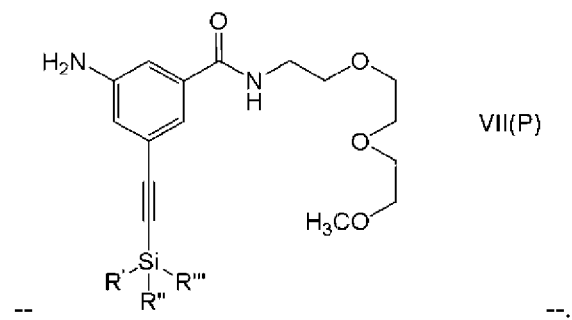
--                                  --.

At column 22, line 25, please replace: